(12) United States Patent
Marton et al.

(10) Patent No.: US 7,569,343 B2
(45) Date of Patent: Aug. 4, 2009

(54) METHODS TO ASSESS QUALITY OF MICROARRAYS

(75) Inventors: Matthew Marton, Seattle, WA (US); Michael Meyer, San Diego, CA (US); Allan Jones, Kirkland, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 111 days.

(21) Appl. No.: 10/520,031

(22) PCT Filed: Jun. 27, 2003

(86) PCT No.: PCT/US03/20504

§ 371 (c)(1),
(2), (4) Date: Aug. 15, 2005

(87) PCT Pub. No.: WO2004/003233

PCT Pub. Date: Jan. 8, 2004

(65) Prior Publication Data

US 2006/0166199 A1    Jul. 27, 2006

Related U.S. Application Data

(60) Provisional application No. 60/392,629, filed on Jun. 28, 2002.

(51) Int. Cl.
*C12Q 1/68* (2006.01)
(52) U.S. Cl. .......................................................... 435/6
(58) Field of Classification Search ....................... None
See application file for complete search history.

(56) References Cited

U.S. PATENT DOCUMENTS

| | | | |
|---|---|---|---|
| 5,143,854 A | 9/1992 | Pirrung et al. | |
| 5,489,678 A | 2/1996 | Fodor et al. | |
| 5,510,270 A | 4/1996 | Fodor et al. | |
| 5,556,752 A | 9/1996 | Lockhart et al. | |
| 5,578,832 A | 11/1996 | Trulson et al. | |
| 5,959,098 A | 9/1999 | Goldberg | |
| 6,028,189 A | 2/2000 | Blanchard | |
| 6,040,138 A * | 3/2000 | Lockhart et al. ................ | 435/6 |
| 6,130,046 A * | 10/2000 | Hubbell et al. .................. | 435/6 |
| 6,197,506 B1 | 3/2001 | Fodor et al. | |
| 6,232,072 B1 * | 5/2001 | Fisher ............................ | 435/6 |
| 6,245,518 B1 * | 6/2001 | Baier ............................. | 435/6 |
| 6,248,878 B1 | 6/2001 | Matulic-Adamic et al. | |
| 6,258,593 B1 | 7/2001 | Schembri et al. | |
| 6,346,413 B1 | 2/2002 | Fodor et al. | |
| 6,362,323 B1 | 3/2002 | Usman et al. | |
| 6,713,257 B2 | 3/2004 | Shoemaker et al. | |

FOREIGN PATENT DOCUMENTS

| | | |
|---|---|---|
| EP | 0 955 085 A2 | 11/1999 |
| EP | 1 179 368 A2 | 2/2002 |
| GB | 2 355 716 A | 5/2001 |
| WO | WO 89/02439 | 3/1989 |
| WO | WO 98/41531 | 9/1998 |
| WO | WO 99/39817 A1 | 8/1999 |
| WO | WO 99/42813 A | 8/1999 |
| WO | WO 01/36682 | 5/2001 |
| WO | WO 01/62377 A2 | 8/2001 |

OTHER PUBLICATIONS

Blanchard "Synthetic DNA Arrays in Genetic Engineering" 1998, vol. 20 111-123.
Blanchard et al. "Sequence to array: probing the genome's secrets" 1996, Nat Biotechnol 14(13):1649.
Blanchard et al "High-density oligonucleotide arrays" 1996, Biosensors & Bioelectronics 11(7-Jun):687-690.
Cload et al. "Polyether Tethered Oligonucleotide Probes" 1991, J Am Chem Soc 113:6324-6326.
DeRisi et al. "Exploring the metabolic and genetic control of gene expression on a genomic scale" 1997, Science 278(5338):680-6.
Durand et al. "Circular dichroism studies of an oligodeoxyribonucleotide containing a hairpin loop made of a hexaethylene glycol chain: conformation and stability" 1990, Nucleic Acids Res 18(21):6353-6359.
Ferentz et al. "Disulfide Cross-Linked Oligonucleotides" 1991, J Am Chem Soc 113:4000-4002.
Fodor et al. "Light-directed, spatially addressable parallel chemical synthesis" 1991, Science 251(4995):767-773.
Goffeau et al. "Life with 6000 genes" 1996, Science 274(5287):546-567.
Gygi et al. "Quantitative analysis of complex protein mixtures using isotope-coded affinity tags" 1999, Nat Biotechnol 17(10):994-999.
Haab et al. "Protein microarrays for highly parallel detection and quantitation of specific proteins and antibodies in complex solutions" 2001, Genome Biol 2(2):RESEARCH0004.1-RESEARCH0004.13.
Holmes et al. "The use of light-directed combinatorial peptide synthesis in epitope mapping" 1995, Biopolymers 37(3):199-211.
Hughes et al. "Expression profiling using microarrays fabricated by an ink-jet oligonucleotide synthesizer" 2001, Nat Biotechnol 19(4):342-347.
Jacobs et al. "Combinatorial chemistry—applications of light-directed chemical synthesis" 1994, Trends Biotechnol 12(1):19-26.
Jaschke et al. "Automated Incorporateion of Polyethylene Glycol into Synthetic" 1993, Tetrahedron Letters 34(2):301-304.
Lockhart et al. "Expression monitoring by hybridization to high-density oligonucleotide arrays" 1996, Nat Biotechnol 14(13):1675-1680.
Ma et al. "Design and synthesis of RNA miniduplexes via a synthetic linker approach" 1993, Biochemistry 32(7):1751-1758.

(Continued)

*Primary Examiner*—Young J Kim
(74) *Attorney, Agent, or Firm*—Jones Day

(57) ABSTRACT

The present invention relates to methods and compositions for assessing the quality of microarrays. In particular, the invention relates to the use of quality control probes that are synthesized on the microarray monomer by monomer in a step-by-step synthesis. By assessing the degree of signal from the quality control probes and determining their deviation from expected signal intensities, the quality of microarray synthesis can be ascertained. The invention further relates to a method of detecting defects occurring during storage or processing of the microarray. The invention further relates to a method of using a computer to identify microarrays that have had a defect or defects during synthesis, storage, or processing.

18 Claims, 20 Drawing Sheets

OTHER PUBLICATIONS

Maskos et al. "Oligonucleotide hybridizations on glass supports: a novel linker for oligonucleotide synthesis and hybridization properties of oligonucleotides synthesised in situ" 1992, Nucleic Acids Res 20(7):1679-1684.

Ma et al. "Design and synthesis of RNA miniduplexes via a synthetic linker approach. 2. Generation of covalently closed, double-stranded cyclic HIV-1 TAR RNA analogs with high Tat-binding affinity" 1993, Nucleic Acids Res 21(11):2585-2589.

McCurdy et al., "Deoxyoligonucleotides with Inverted Polarity: Synthesis and Use in Triple-Helix Formation," 1991, Nucleosides & Nucleotides 10: 287-290.

Ono et al. "DNA triplex formation of oligonucleotide analogues consisting of linker groups and octamer segments that have opposite sugar-phosphate backbone polarities" 1991, Biochemistry 30(41):9914-2.

Pease et al. "Light-generated oligonucleotide arrays for rapid DNA sequence analysis" 1994, Proc Natl Acad Sci U S A 91(11):5022-5026.

Richardson et al. "Tethered Oligonucleotide Probes. A Strategy for the Recognition of Structured RNA" 1991, J Am Chem Soc 113(5109):5111.

Schena et al. "Quantitative monitoring of gene expression patterns with a complementary DNA microarray" 1995, Science 270(5235):467-470.

Seela et al. "Oligodeoxyribonucleotides containing 1,3-propanediol as nucleoside substitute" 1987, Nucleic Acids Res 15(7):3113-3129.

Shalon et al. "A DNA microarray system for analyzing complex DNA samples using two-color fluorescent probe hybridization" 1996, Genome Res 6(7):639-645.

Takeshita et al. "Oligodeoxynucleotides containing synthetic abasic sites. Model substrates for DNA polymerases and apurinic/apyrimidinic endonucleases" 1987, J Biol Chem 262(21):10171-10179.

Hubbell et al., 1999, "Fidelity Probes for DNA Arrays," Proceedings of the International Conference on Intelligent Systems for Molecular Biology, August 6; 113-117.

Supplementary European search report dated May 16, 2007 for European Patent Application No. 03 762 218.0—1222.

* cited by examiner

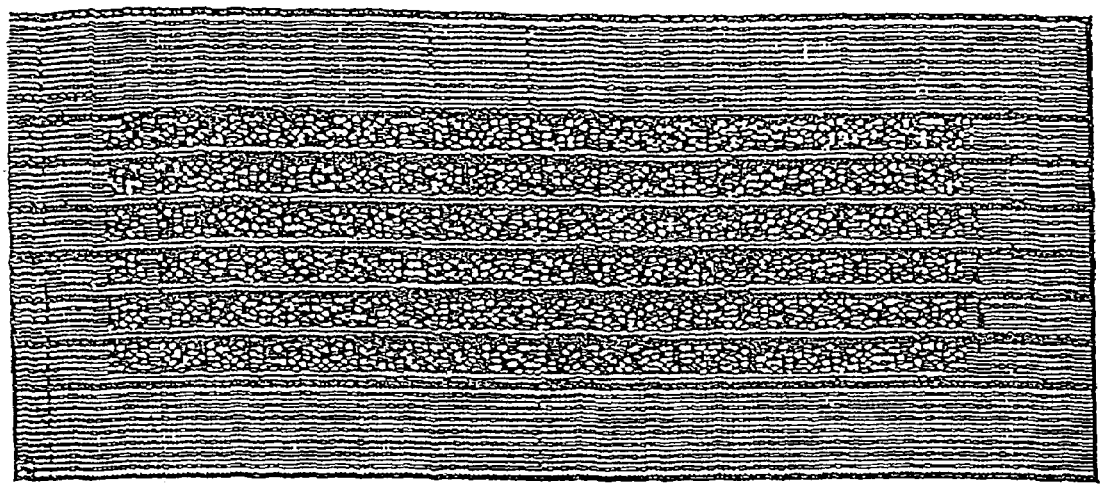
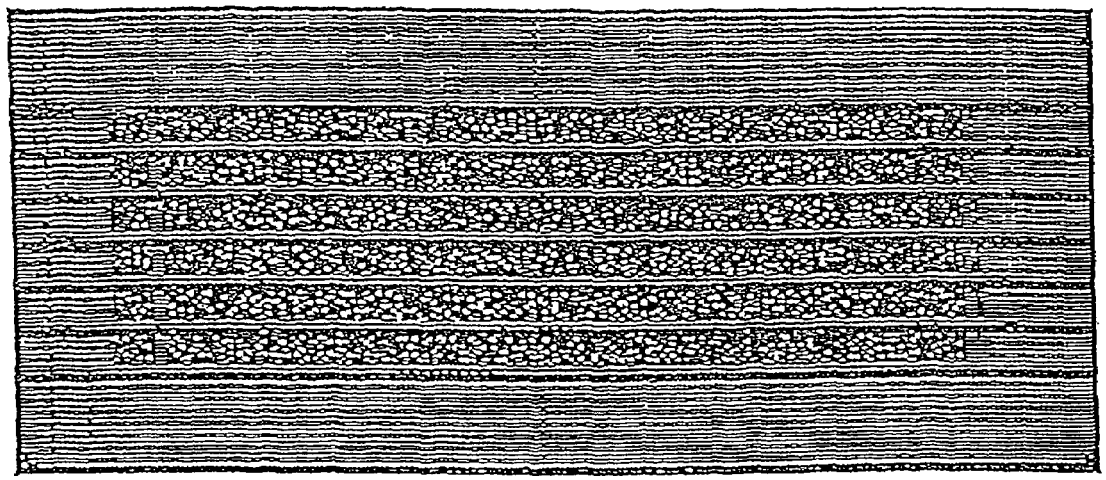
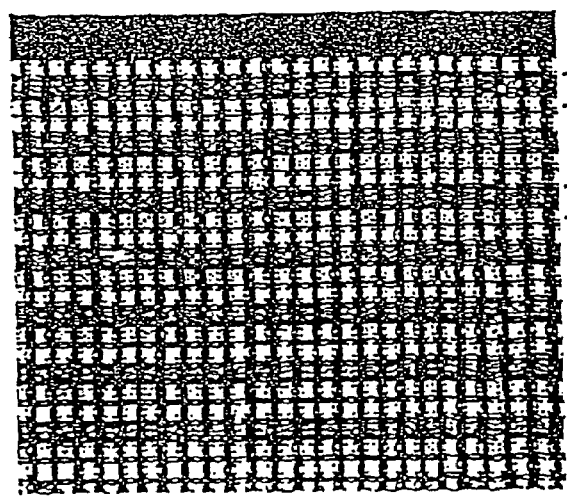
FIGS. 7A-7B

METHODS TO ASSESS QUALITY OF MICROARRAYS This application claims priority to U.S. Provisional Application Ser. No. 60/392,629, filed Jun. 28, 2002, which is incorporated herein by reference in its entirety.

1. FIELD OF THE INVENTION

The present invention relates to methods and compositions for assessing the quality of microarray synthesis. The invention further relates to a method of detecting defects occurring during storage or processing of the microarray. In particular, the invention relates to the use of quality control probes that are synthesized on the microarray for assessing microarray quality. The invention further relates to a method of using a computer to identify microarrays that have a defect or defects, e.g., arising during synthesis, storage, or processing.

2. BACKGROUND OF THE INVENTION

DNA array technologies have made it possible, inter alia, to monitor the expression levels of a large number of genetic transcripts at any one time (see, e.g., Schena et al., 1995, *Science* 270:467-470; Lockhart et al., 1996, *Nature BioTechnology* 14:1675-1680; Blanchard et al., 1996, *Nature BioTechnology* 14:1649; Shoemaker et al., U.S. patent application Ser. No. 09/724,538, filed on Nov. 28, 2000). DNA array technologies have also found applications in gene discovery, e.g., in identification of exon structures of genes (see, e.g., Shoemaker et al., U.S. patent application Ser. No. 09/724,538, filed on Nov. 28, 2000; Meltzer, 2001, *Curr. Opin. Genet. Dev.* 11(3):258-63; Andrews et al., 2000, *Genome Res.* 10(12):2030-43; Abdellatif, 2000, *Circ. Res.* 86(9):919-20; Lennon, 2000, *Drug Discov. Today* 5(2):59-66; Zweiger, 1999, *Trends Biotechnol.* 17(11):429-36).

By simultaneously monitoring tens of thousands of genes, microarray technologies have allowed, inter alia, genome-wide analysis of mRNA expression in a cell or a cell type or any biological sample. Aided by sophisticated data management and analysis methodologies, the transcriptional state of a cell or cell type as well as changes of the transcriptional state in response to external perturbations, including but not limited to drug perturbations, can be characterized on the mRNA level (see, e.g., U.S. Pat. No. 6,203,987; Stoughton et al., International Publication No. WO 00/24936 (published May 4, 2000); Stoughton et al., International Publication No. WO 00/39336 (published Jul. 6, 2000); Friend et al., International Publication No. WO 00/24936 (published May 4, 2000)). Applications of such technologies include, for example, identification of genes which are up regulated or down regulated in various physiological states, particularly diseased states. Additional exemplary uses for DNA arrays include the analyses of members of signaling pathways, and the identification of targets for various drugs. See, e.g., Friend and Hartwell, International Publication No. WO 98/38329 (published Sep. 3, 1998); Friend and Stoughton, International Publication No. WO 99/59037 (published Nov. 18, 1999); U.S. Pat. Nos. 6,132,969; 5,965,352; 6,218,122.

A microarray is an array of positionally-addressable binding (e.g., through hybridization) sites on a support. Each of such binding sites comprises a plurality of biopolymer molecules of a probe bound to a predetermined region on the support. Microarrays can be fabricated in a number of ways, including immobilization of pre-synthesized probes on the support or the in situ synthesis of probes on the support. For example, immobilization of pre-synthesized probes can be done robotically as described in DeRisi et al. (1997, *Science* 278(5338):680-6) or by inkjet. In situ synthesis can be accomplished by different means, including using inkjet technology or by light-activated synthesis (Holmes et al., 1995, *Biopolymers* 37(3): 199-211; Jacobs et al., 1994, *Trends Biotechnol.* 12(1): 19-26; and Fodor et al., 1991, *Science* 251 (4995):767-73). In either case of in situ synthesis, chemical reactions take place on the support in which a monomer or monomers are added to the biopolymer. As the biopolymer chain grows, however, there is a chance that one or more of the synthesis cycles may fail (either fully or partially) thereby producing a probe that lacks one or more of the intended monomers. Synthesis efficiency depends on multiple factors including reagent purity, reaction time, correct alignment of the inkjet head, etc. Defects in any of these processes can result in inefficient addition of a monomer or monomers to the growing biopolymer chain.

In addition, in the case of an inkjet-synthesized microarray, a synthesis defect may also occur when one of the nozzles of the inkjet head fails to deliver a reagent properly (e.g., if the nozzle becomes temporarily or permanently obstructed). A nozzle failure refers to any malfunction of an individual ink jet nozzle. If a nozzle fails to deliver the desired solution required for biopolymer addition, it is sometimes referred to as being "clogged." A nozzle failure can occur at any point during microarray synthesis. A failure at the beginning of the synthesis may be due to insufficient priming of new reagents through the nozzles. A nozzle failure can also occur after the printing of a set of microarrays has begun if, e.g., there are trapped air bubbles or particulates. Nozzle failures can be detected and corrected before a microarray is synthesized. Before the start of each synthesis batch and at the end of each synthesis batch every nozzle on the printhead can be tested to make sure that it is properly functioning. This can be done by placing a clean substrate on top of the head assembly before forcing each nozzle to extrude a small amount of liquid. If all nozzles are working properly, there will be a drop of liquid corresponding to each nozzle. If, however, one or more nozzles are malfunctioning, the drops corresponding to those nozzle positions will be missing. Because of the small size of the drops, a nozzle failure can be overlooked occasionally due to human error, and an array will be synthesized that shows evidence of a nozzle failure. Currently there exists a need for a more reliable method to determine if synthesis failures have occurred and, if so, where and when they happened during the course of microarray synthesis. Whereas it is possible to perform quality control on pre-synthesized probes by conventional DNA sequencing, by mass spectroscopy, or by other means, methods to assess the quality of probes synthesized in situ are lacking.

This application describes a method designed to assess the quality of microarray synthesis. The herein disclosed invention describes methods for the design and production of quality control probes on microarrays and methods for analysis of the information obtained from microarray processing that permit the determination of the overall quality of synthesis as well as the identity of the synthesis cycle most likely to have been defective. This invention also includes a database that contains information concerning the position and identity of the quality control probes on microarrays.

Citation or discussion of a reference herein shall not be construed as an admission that such is prior art to the present invention.

3. SUMMARY OF THE INVENTION

The present invention relates to methods and compositions to assess the quality of microarrays where the biopolymer probes are synthesized on the array substrate monomer by monomer in a step-by-step synthesis. In particular, failures or inefficiencies in the deposition of individual synthesis cycles of the microarray are detected through the inclusion of quality control probes on the microarray. The quality control probes are synthesized onto the microarray concurrently with the other biopolymer probes and thus would also be subject to any synthesis failures or inefficiencies that may occur. By assessing the degree of signal from the quality control probes and determining their deviation from expected signal intensities, the quality of microarray synthesis can be ascertained.

In one embodiment, each group of quality control probes comprises the same redetermined binding sequence for which a binding partner exists in or is introduced into the sample to be contacted with the microarray for analysis. The synthesis of the predetermined binding sequence in each quality control probe is initiated during the step-by-step synthesis at sequential cycles of synthesis. By assessing the degree of binding of a biopolymer capable of binding to the predetermined binding sequence of the quality control probe, the quality of microarray synthesis can be determined. In another embodiment, the quality control probes do not comprise a predetermined binding sequence. A detectable signal is generated by the quality control probe itself rather than a labeled binding partner binding to the predetermined binding sequence. This can be accomplished by, e.g., incorporation of one or more labeled monomers into the quality control probe, staining of the quality control probe with a fluorescent dye, etc.

In a preferred embodiment, the invention relates to methods of detecting synthesis failures on a oligonucleotide microarray. In a more preferred embodiment, the invention relates to methods of detecting synthesis defects including nozzle failures during the synthesis of an ink jet oligonucleotide microarray. In addition to synthesis failures, other defects that affect microarray quality can also be detected, e.g., those due to degradation of probes during storage or processing of the microarray.

The invention provides a positionally addressable array comprising a substrate to which are attached a plurality of different biopolymer probes, said different biopolymer probes in said plurality being situated at different positions on said surface and being the product of a step-by-step synthesis of said biopolymer probes on said substrate, said plurality of different binding probes comprising a plurality of quality control probes, the synthesis of said quality control probe having been initiated during said step-by-step synthesis at sequential cycles of synthesis. Each quality control probe in said plurality comprising a predetermined binding sequence preferably comprises the same predetermined binding sequence or alternatively a different predetermined binding sequence but with the same binding specificity or similar binding characteristics (e.g., bind to their respective binding partner with similar intensities under the same binding conditions). In one embodiment, predetermined binding sequences of different lengths can be used (e.g., a 25mer and a 24mer).

In one specific embodiment of the array, the sequence of each said quality control probe of said plurality consists of said predetermined binding sequence.

In another specific embodiment, the plurality of quality control probes comprise a second sequence consisting of a chemical structure contiguous with said predetermined binding sequence, wherein at least some of the quality control probes differ from other of the quality control probes in length of said chemical structure. In a specific embodiment, the chemical structure is a sequence of number 0 to N monomers contiguous with said predetermined binding sequence, and where N is a whole number equal to or greater than 1. In a specific embodiment, the biopolymer probes are oligonucleotides, said predetermined sequence consists of 25 nucleotides, and said biopolymer probes that are not said quality control probes consist of 60 nucleotides. In a specific embodiment, N is not greater than the number of monomers in said biopolymer probes on the array that are not said quality control biopolymer probes minus the number of monomers in said predetermined binding sequence. In another specific embodiment, the quality control probes comprise a greater number of monomers than biopolymer probes on the array that are not said quality control biopolymer probes. In a further specific embodiment, an array comprises 3, 10, 30, 60 or more of said quality control probes that differ in N. A particular embodiment is wherein N is 0, 20, and 35, respectively, for different quality control probes.

In yet another specific embodiment, the plurality of quality control probes comprise
(i) quality control probes whose sequence consists of said predetermined sequence; and
(ii) quality control probes that comprise a second sequence of number 0 to N monomers contiguous with said predetermined binding sequence, wherein at least some of said quality control probes differ from other of said quality control probes in the number of said monomers, and where N is a whole number equal to or greater than 1.

In various specific embodiments, the biopolymer probes are nucleic acids, proteins, or antibodies. Preferably the predetermined binding sequence is in the range of 10-40 nucleotides in length, and more preferably, is 25 nucleotides in length. In a specific embodiment, the predetermined binding sequence is SEQ ID NO:1 or SEQ ID NO:2 or a complement thereof.

In one embodiment, the biopolymer probes consist of a sequence in the range of 20-100 nucleotides.

Preferably, the predetermined binding sequence of the quality control biopolymer probe is between 10-75% of the length of the length of the biopolymer probes on the array that are not quality control probes.

In a specific embodiment, the predetermined binding sequence consists of 25 monomers, and the biopolymer probes on the array that are not said quality control probes consist of 60 monomers.

The invention also provides a method of determining if a positionally-addressable biopolymer array has a synthesis defect comprising the following steps in the order stated:
a) contacting an array of the invention with a sample comprising a binding partner that binds said predetermined binding sequence;
b) detecting or measuring binding between two or more of said quality control probes and said binding partner in the sample; and
c) comparing binding of said two or more of said quality control probes, wherein if said binding is similar, the absence of a synthesis defect between said sequential cycles of synthesis of said array is indicated.

The invention further provides a method of determining if a positionally-addressable biopolymer array has a synthesis defect comprising the following steps in the order stated:
a) contacting an array as described above containing the quality control probes comprising the 0 to N monomer contiguous sequence, with a sample comprising a binding partner that binds said predetermined binding sequence;

b) detecting or measuring binding between (i) two or more of said quality control probes that differ in the number of said monomers; and (ii) said binding partner in the sample; and c) comparing binding of said two or more of said quality control probes, wherein if said binding is similar, the absence of a synthesis defect between said sequential cycles of synthesis used to synthesize said two or more quality probes is indicated.

The invention further provides a method of determining if a positionally-addressable biopolymer array has a synthesis defect caused by a nozzle failure comprising the following steps in the order stated:

a) contacting the array of the invention with a sample comprising a binding partner that binds said predetermined binding sequence, wherein at least a portion of said plurality of quality control probes is arranged in a periodicity of P and wherein said array is synthesized by step-by-step synthesis using an inkjet printhead with P nozzles, wherein P is a whole number equal to or greater than 1;

b) detecting or measuring binding between two or more of said quality control probes and said binding partner in the sample; and c) comparing binding of said two or more of said quality control probes in a periodicity of P, wherein if said binding is similar, the absence of a nozzle defect is indicated.

In the foregoing methods, the comparing step can comprise determining the binding ratio of two of said two or more quality control probes, wherein said binding ratio is the amount of binding of a first of said two quality control probes with said binding partner, divided by the amount of binding of a second of said two quality control probes with said binding partner, and wherein said binding ratio between 0.5 and 2.0 indicates the absence of said synthesis defect.

In a specific embodiment, the foregoing methods further comprise before step (a) the step of synthesizing said array.

In a specific embodiment, the sample comprises (i) total cellular RNA or mRNA from one or more cells or a plurality of nucleic acids derived therefrom, and (ii) said binding partner, wherein said binding partner is not expressed by said cells.

The invention also provides a method of making a positionally-addressable array of a plurality of different biopolymer probes comprising synthesizing said plurality of different biopolymer probes on a substrate from monomers using a step-by-step synthesis such that each of said different biopolymer probes is attached to said substrate at a different position on said substrate, wherein said plurality of different biopolymer probes comprise a plurality of quality control probes, each quality control probe in said plurality comprising the same predetermined binding sequence, wherein the synthesis of said predetermined binding sequence in each of said quality control probes is initiated during said step-by-step synthesis at sequential cycles of synthesis. The array thus made can have the characteristics described above.

The invention further provides an oligonucleotide comprising a nucleotide sequence of SEQ ID NO:1 or SEQ ID NO:2 or the complement thereof.

4. DESCRIPTION OF THE FIGURES

FIG. 1 illustrates an ink jet oligonucleotide microarray that was synthesized with three malfunctioning nozzles. Entire rows corresponding to nozzles 4, 15, and 20 were not synthesized due to nozzle malfunction.

FIGS. 2A-2B schematically illustrate the use of quality control probes with spacers to determine the synthesis quality of an oligonucleotide microarray. (A) The 25 nucleotide long probe was either synthesized directly onto the microarray or was attached to a spacer of varying lengths (i.e., 20 nucleotides or 35 nucleotides). (B) A synthesis error in synthesis cycle 24 is depicted and thus affects the sequence of monomers in the predetermined binding sequence in only the first two quality control probes shown. The solid line depicts the quality control probe and the dashed line depicts the spacer.

FIGS. 3A-3B schematically illustrate the use of staggered start quality control probes to determine the synthesis quality of an oligonucleotide microarray. (A) A series of 25 nucleotide quality control probes are synthesized directly on the microarray staring at synthesis cycle 1 through synthesis cycle 36. The only difference between the quality control probes is the synthesis cycle at which synthesis begins. (B) A synthesis error in synthesis cycle 29 is depicted and thus only affects the quality control probes in which synthesis cycle 29 was actually used to add a monomer to the sequence of the quality control probe (i.e., those quality control probes that begin synthesis at synthesis cycles 5-29). The bold line depicts the quality control probe and the thin line depicts synthesis cycles that had no monomer deposited.

FIGS. 4A-4B illustrate the use of quality control probes comprising a spacer to determine the synthesis quality of an oligonucleotide microarray when there were no known or detectable synthesis defects during oligonucleotide microarray synthesis. (A) Microarray image after hybridization to a fluorescently labeled oligonucleotide that hybridized to the quality control probes. (B) Higher magnification of the microarray in (A) that depicts the positions of the 25mer, 40mer, and 60mer.

FIGS. 5A-5B illustrate the use of quality control probes comprising a spacer to determine the synthesis quality of an oligonucleotide microarray when the first synthesis cycle was intentionally skipped during oligonucleotide microarray synthesis. (A) Microarray image after hybridization to a fluorescently labeled oligonucleotide that hybridized to the quality control probe. (B) Higher magnification of the microarray in (A) that depicts the positions of the 25 mer, 40 mer, and 60 mer.

FIGS. 6A-6B illustrate the use of quality control probes comprising a spacer to determine the synthesis quality of an oligonucleotide microarray when the first and second synthesis cycle were intentionally skipped during oligonucleotide microarray synthesis. (A) Microarray image after hybridization to a fluorescently labeled oligonucleotide that hybridized to the quality control probe. (B) Higher magnification of the microarray in (A) that depicts the positions of the 25 mer, 40 mer, and 60 mer.

FIGS. 7A-7B illustrate the use of quality control probes comprising a spacer to determine the synthesis quality of an oligonucleotide microarray when the thirty sixth synthesis cycle was intentionally skipped during oligonucleotide microarray synthesis. (A) Microarray image after hybridization to a fluorescently labeled oligonucleotide that hybridized to the quality control probe. (B) Higher magnification of the microarray in (A) that depicts the positions of the 25 mer, 40 mer, and 60 mer.

FIGS. 8A-8B illustrate the use of quality control probes comprising a spacer to determine the synthesis quality of an oligonucleotide microarray when the thirty fourth and thirty fifth synthesis cycles were intentionally skipped during oligonucleotide microarray synthesis. (A) Microarray image after hybridization to a fluorescently labeled oligonucleotide that hybridized to the quality control probe. (B) Higher magnification of the microarray in (A) that depicts the positions of the 25 mer, 40 mer, and 60 mer.

FIGS. 9A-9B illustrate the use of quality control probes comprising a spacer to determine the synthesis quality of an oligonucleotide microarray when there was inefficient synthesis in the first twenty two synthesis cycles during oligonucleotide microarray synthesis. (A) Microarray image after hybridization to a fluorescently labeled oligonucleotide that hybridized to the quality control probe. (B) Higher magnification of the microarray in (A) that depicts the positions of the 25 mer, 40 mer, and 60 mer.

FIGS. 10A-10B illustrate the use of staggered start quality control probes to determine the synthesis quality of an oligonucleotide microarray when there was inefficient synthesis in the first and second synthesis cycles during oligonucleotide microarray synthesis. (A) Microarray image after hybridization to a fluorescently labeled oligonucleotide that hybridized to the quality control probe. (B) The mean fluorescence intensity plot of the quality control probes at each synthesis cycle.

FIGS. 11A-11B illustrate the use of staggered start quality control probes to determine the synthesis quality of an oligonucleotide microarray when there was inefficient synthesis in the first five synthesis cycles during oligonucleotide microarray synthesis. (A) Microarray image after hybridization to a fluorescently labeled oligonucleotide that hybridized to the quality control probe. (B) The mean fluorescence intensity plot of the quality control probes at each synthesis cycle.

FIGS. 12A-12B illustrate the use of staggered start quality control probes to determine the synthesis quality of an oligonucleotide microarray when there was inefficient synthesis in the first eight synthesis cycles during oligonucleotide microarray synthesis. (A) Microarray image after hybridization to a fluorescently labeled oligonucleotide that hybridized to the quality control probe. (B) The mean fluorescence intensity plot of the quality control probes at each synthesis cycle.

FIGS. 13A-13B illustrate the use of staggered start quality control probes to determine the synthesis quality of an oligonucleotide microarray when there was inefficient synthesis in the forty fifth to sixtieth synthesis cycles during oligonucleotide microarray synthesis. (A) Microarray image after hybridization to a fluorescently labeled oligonucleotide that hybridized to the quality control probe. (B) The mean fluorescence intensity plot of the quality control probes at each synthesis cycle.

FIGS. 14A-14B illustrate the increased sensitivity of a single-deletion quality control probe. Microarray with synthesis defects in the thirty fourth and thirty fifth synthesis cycles were synthesized with quality control probes either (A) without or (B) with an intentional single deletion in the predetermined binding sequence. The labeled reverse complement of the full-length 25 nucleotide predetermined binding sequence was used to hybridize with each microarray. The mean fluorescence intensity plot of the quality control probes at each synthesis cycle was determined for each microarray.

Figure 1:
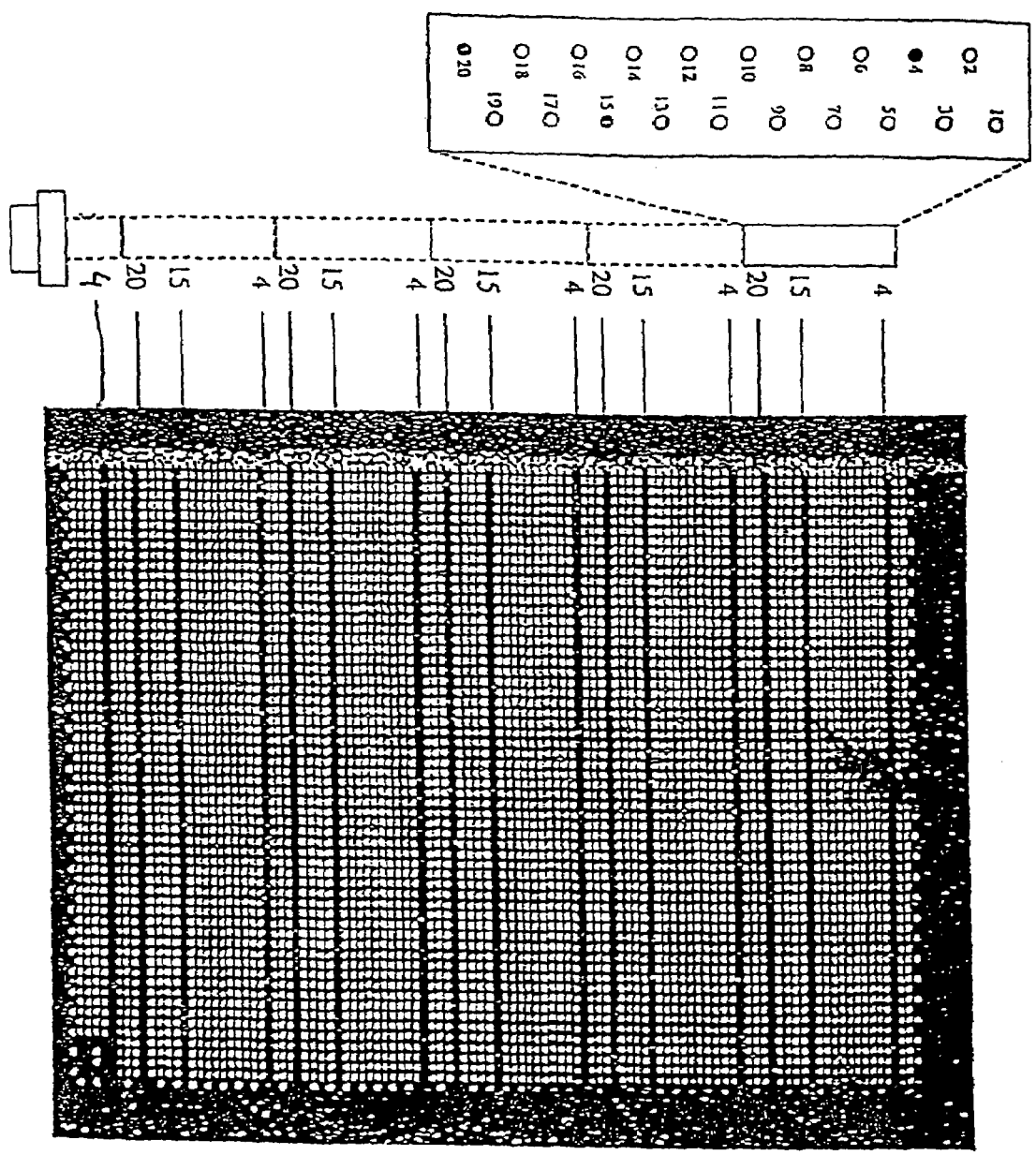

FIGS. 17A-17D schematically illustrate a microarray with quality control probes attached to the substrate. (A) outer gridline, (B) diagonal gridline, (C) internal cluster, (D) corner cluster.

5. DETAILED DESCRIPTION OF THE INVENTION

The object of the present invention is to assess the quality of microarray synthesis for arrays where the biopolymer probes are synthesized on the array substrate monomer by monomer in a step-by-step synthesis. This object is fulfilled by the synthesis of quality control probes on the microarray to be assessed. The quality control probes are synthesized in the same manner as, and in conjunction with, the other biopolymer probes on the microarray.

The quality control probes may comprise a predetermined binding sequence. This predetermined binding sequence has a binding partner that can be used to detect the presence of the predetermined binding sequence during microarray processing. In some embodiments, the quality control probe also comprises a chemical structure contiguous with the predetermined binding sequence (such chemical structure referred to herein as a "spacer"). The spacer is preferably a polymer (e.g., a sequence) of additional monomers attached to (contiguous with) the predetermined binding sequence. Upon completion of microarray synthesis, the quality control probes are detected by binding to a labeled binding partner. The degree of binding is quantified for each quality control probe and compared to the binding intensities of other quality control probes. Similar binding intensities indicate synthesis was equally efficient throughout the synthesis.

In another specific embodiment, the quality control probes do not comprise a predetermined binding sequence. In such an embodiment, the signal observed with this type of quality control probe is emitted either by 1) the monomers that make up the quality control probe directly or 2) a label (e.g., a dye) that interacts with or is attached to the monomers that make up the quality control probe. Deviation from the expected binding intensities indicate a defect in the array, e.g., due to a synthesis defect, or degradation during storage or processing.

Although the invention is generally described in terms of the use of one group of quality control probes, it will be understood that different groups of quality control probes can also be used on a single microarray. The different groups of quality control probes may have different predetermined binding sequences or may be a mixture of quality control probes with and without predetermined binding sequences. The quality control probes may also be a mixture of different lengths (e.g., a mixture of quality control probes comprising predetermined binding sequences of 25 mers or 24 mers).

5.1 Quality Control Probes with Predetermined Binding Sequences 5.1.1 Predetermined Binding Sequence Quality control probes with predetermined binding sequences are biopolymers that comprise a predetermined binding sequence and do not interfere with the results of the intended microarray processing. So as to avoid cross-reactivity in binding, biopolymers of the sample to be assayed should not bind to the quality control probes on the microarray. Also, the reverse complement of the predetermined binding sequence used to bind to and detect the quality control probes should not bind to the test probes (i.e., probes on the microarray designed to bind biopolymers of the sample) on the microarray. In the method of the present invention, the quality control probe is made according to the particular requirements of the combination of origin, preparation, and processing of the sample to be analyzed on the microarray to be synthesized. Preferably, wherein the sample to be analyzed on the microarray comprises naturally occurring nucleic acids or proteins, the predetermined binding sequence of the quality control probes is not present or is not known to be present in any naturally occurring nucleic acid or is not known to encode any naturally occurring protein, respectively. In another embodiment, the predetermined binding sequence of the quality control probes is not present or is not known to be present in the sample. This is done to reduce the likelihood that the predetermined binding sequence will be cross-reactive. Cross-reactivity indicates that a biopolymer has the ability to interact (e.g., hybridize or bind) with more than one other biopolymer present during microarray processing. For example, during processing of an oligonucleotide microarray, if the predetermined binding sequence hybridizes with its complementary nucleic acid as well as with a different sequence in the biological sample then the probe is said to be cross-reactive. Cross-reactivity in a probe is undesirable, since it could alter the signal intensities observed from sample processing and affect the assessment of microarray synthesis quality.

In one embodiment, the potential sequence of monomers that make up the predetermined binding sequence can be identified from a pool of randomly synthesized sequences. These potential predetermined binding sequences can then be assayed for their cross-reactivity with the biological sample to be processed or probes designed to detect naturally occurring sequences in the biological sample during processing. Preferably, predetermined binding sequences that are not substantially cross-reactive with biopolymers being assayed in the sample are used in quality control probes. Thus, at the time of microarray synthesis, the sequence of the quality control probes is known although the sequence is random in that it had initially been the product of a random synthesis. The random sequences are biopolymer residues (e.g., nucleotide or amino acid residues) that are generated without a preplanned specific design as to the actual resulting sequence, i.e., when a monomer (e.g., nucleotide, amino acid) is said to be random it is unpredictable what monomer will occur at that residue. The random sequences can be synthesized by an unbiased synthesis scheme wherein each possible residue has an equal chance of being incorporated into the biopolymer at each position. Alternatively, the random sequences can be synthesized by a biased synthesis scheme wherein certain positions in the biopolymer have an increased chance of having one residue over another. Additionally, a combination of unbiased and biased synthesis methods can be used to synthesize any one biopolymer. In one embodiment, sequences on either end or at internal positions may be added to the predetermined binding sequence for the purposes of facilitating standard molecular biological manipulations. Once generated, the sequence of the predetermined binding sequence if generated randomly is determined. Preferably, the sequence is then tested for cross-reactivity, and recorded for future use. For each microarray one or more of the predetermined binding sequences that have been empirically determined to be noncross-reactive are then synthesized on the microarray to allow for future assessment of synthesis quality or other non-synthesis defects in the array.

In another embodiment, the predetermined binding sequence can be a naturally occurring sequence that is not endogenous to the sample that is to be processed on the microarray. For example, if the sample is from a eukaryotic source, then a bacterial sequence (or fragment thereof) can be used as the predetermined binding sequence. Cross-reactivity could be assessed as a precautionary measure.

Accordingly, where the binding partner to the predetermined sequence of the quality control probes is not endogenously present in the sample to be assayed for binding to the microarray, the binding partner to the predetermined binding sequence in the quality control probe is introduced into the sample at any time prior to or during contacting of the sample with the microarray. In one embodiment, the binding partner is added to the sample during sample processing. In a more preferred embodiment, the binding partner is added to the sample immediately prior to contact of the sample with the microarray.

The predetermined binding sequence can be made of any type of biological macromolecule; preferably the molecular nature of the quality control probe is consistent with that of the other biopolymer probes on the microarray. For example, the predetermined binding sequence can be composed of nucleotides (i.e., DNA or RNA), amino acids, glycans, saccharides, or small organic molecules.

In one embodiment, the predetermined binding sequence is a nucleic acid, preferably an oligonucleotide, and a nucleic acid microarray is contacted with a sample comprising a nucleic acid comprising a sequence complementary to the predetermined binding sequence under conditions conducive to hybridization, and the amount of hybridization to quality control probes is compared.

In another embodiment, the predetermined binding sequence is a protein (polypeptide or peptide), and a protein microarray is contacted with a sample comprising a binding partner to said protein under conditions conducive to binding, and the amount of binding to quality control probes is compared. In one embodiment, the binding moiety is an epitope recognized by an antibody, preferably a monoclonal antibody. Preferably, epitopes re unique (i.e., not endogenously expressed in cells or tissues that provide protein material for the samples) to minimize cross-reactivity of the antibodies directed to predetermined binding sequence epitopes with sample epitopes during detection.

The length of the predetermined binding sequence can vary depending upon the length of the other biopolymer probes on the microarray used to detect binding partners in the sample to be assessed. Typically, the predetermined binding sequence is composed of a smaller number of monomers than the other biopolymer probes on the microarray. This allows the predetermined binding sequence to represent only a subset of the total monomers that make up the other biopolymer probes on the microarray. As such, multiple predetermined binding sequences are needed to represent each full length biopolymer probe. This allows for different cycles of synthesis to be targeted for inspection by different quality control probes depending upon which cycles of synthesis were used to synthesize the predetermined binding sequence. Binding intensities can be compared between different predetermined binding sequences to ascertain information regarding the different portions of the full length biopolymer probes. The predetermined binding sequence is preferably between 5-95%, 10-75%, 25-65%, 35-60%, 40-55%, or 41-48% of the length of the other biopolymer probes on the microarray. In another embodiment, the predetermined binding sequence is 15 biopolymer residues when the other probes on the microarray are 60 biopolymer residues in length. In another embodiment, the predetermined binding sequence is 25 biopolymer residues when the other probes on the microarray are 60 biopolymer residues in length. The length of the biopolymer probes on the microarray that are not quality control probes, when nucleic acids, is preferably in the range of 10-500 nucleotides, more preferably 10-250, 20-100, 40-80, 50-70 or 60 nucleotides.

5.1.1.1 Predetermined Binding Sequences with Intentional Deletions

In some embodiments, the predetermined binding sequence has an intentional deletion of one or more monomers relative to a sequence that binds a binding partner used to detect the quality control probe during microarray processing. Thus, in a specific embodiment, the predetermined binding sequence has an internal deletion of a nucleotide relative to a sequence perfectly complementary to the nucleic acid used to detect the quality control probe by hybridization. Although this does decrease the signal intensity due to an imperfect binding pair, signal can still be observed. Any additional deletions due to a failure during microarray synthesis would exacerbate the difference between predetermined binding sequence and binding partner and thus serve to drastically reduce the signal observed during microarray processing. In one embodiment, on an oligo microarray, the predetermined binding sequence is a 24 mer (i.e., has one monomer intentionally deleted) and the binding partner is a 25 mer.

In one embodiment, each quality control probe on a microarray comprises a predetermined binding sequence comprising one or more such intentional deletions. In another embodiment, the quality control probes on a microarray are a mixture of those comprising predetermined binding sequences comprising one or more intentional deletions and those comprising predetermined binding sequences with no intentional deletions.

5.1.2 Spacers

In some embodiments, the quality control probes comprise a chemical structure contiguous with the predetermined binding sequence. This chemical structure is referred to herein as a spacer. The spacer is preferably made up of 0 to N monomers (e.g., nucleotides, amino acid residues), where N is a whole number integer equal to or greater than 1. Preferably, the spacers added are less than 75%, less than 50%, less than 25%, less than 20%, less than 15%, less than 10%, less than 5%, or less than 1% of the total sequence of the quality control probe. Spacers can be on one side of the predetermined binding sequence or on both sides. For nucleic acid probes, the spacers can be either 5' or 3' or both 5' and 3' to the predetermined binding sequence. In one embodiment, the spacers are exclusively 3' to the predetermined binding sequence. For protein probes, the spacers can be either amino- or carboxy-terminal or both amino- and carboxy-terminal to the predetermined binding sequence. In a specific embodiment, the spacer is a nucleotide or protein sequence.

In one embodiment, the value of the upper limit of N is determined by the length of the biopolymer probes synthesized on the microarray that are not quality control probes (i.e., those not containing the predetermined binding sequence). The total length of the quality control probe is preferably not greater than the total length of the other biopolymer probes on the microarray. Therefore, in a specific embodiment, N plus the number of monomers in the predetermined binding sequence should equal the total number of monomers in the biopolymer probes on the array that are not quality control probes. In another embodiment, the value of N is not constrained by the length of the biopolymer probes synthesized on the microarray that are not quality control probes (i.e., those not containing the predetermined binding sequence). In this embodiment, quality control probes can be shorter or longer than the other biopolymer probes on the microarray.

Spacers are preferably not cross-reactive with the biopolymer being assayed in the sample. During microarray processing, preferably no signal is detected from the spacer. Additionally, the spacer should not interfere with the signal generated from the predetermined binding sequence binding to its binding partner during microarray processing. In one embodiment, interference with such signal is prevented because the chemical structure that makes up the spacer is modified such that the spacer is not able to bind a binding partner. For example, modified nucleic acids that are not competent to hybridize can be used in spacers and will be non-cross-reactive, e.g., abasic nucleotides (i.e., moieties lacking a nucleotide base, but having the sugar and phosphate portions) (see generally U.S. Pat. No. 6,248,878; Takeshita et al, 1987, *J. Biol. Chem.* 262:10171; abasic nucleotides are commercially available from Glen Research in Sterling, Va.).

In another embodiment, spacers can be made of a chemical moiety that is different from the monomers present in the other biopolymer probes on the microarray not dedicated to quality control and/or the monomers that make up the predetermined binding sequence. For example, on a nucleotide microarray, spacers can be made from non-nucleotide moieties such as polyether, polyamine, polyamide, or polyhydrocarbon compounds. Specific examples include those described by Seela and Kaiser, 1990, *Nucleic Acids Res.* 18:6353; Seela and Kaiser, 1987, *Nucleic Acids Res.* 1987, 15:3113; Cload and Schepartz, 1991, *J. Am. Chem. Soc.* 113: 6324; Richardson and Schepartz, 1991, *J. Am. Chem. Soc.* 113:5109; Ma et al., 1993, *Nucleic Acids Res.* 21:2585; Ma et al., 1993, *Biochemistry* 32:1751; Durand et al., 1990, *Nucleic Acids Res.* 18:6353; McCurdy et al., 1991, *Nucleosides & Niicleotides* 10:287; Jaschke et al., 1993, Tetrahedron Lett. 34:301; Ono et al., 1991, *Biochemistry* 30:9914; Ferentz and Verdine, 1991, *J. Am. Chem. Soc.* 113:4000; U.S. Pat. No. 6,362,323; International Publication No. WO 89/02439.

Preferably, once generated, the entire quality control probe sequence is determined, tested for cross-reactivity, and recorded for future use.

5.2 Quality Control Probes Without Predetermined Binding Sequences

In some embodiments quality control probes do not have predetermined binding sequences but are made exclusively of a spacer. Signals observed with this type of quality control probes are emitted either 1) directly from the chemical structure (e.g., the monomers) that make up the quality control probe or 2) indirectly through the use of a labeled dye which interacts with the chemical structure (e.g., the monomers) that make up the quality control probe. These types of quality control probes can give off a signal without the use of a labeled binding partner.

Thus, in one embodiment, quality control probes are synthesized with labeled monomers. The labeled monomers can be, for example, fluorescently labeled (e.g., Cy3, Cy5) nucleotides or fluorescently labeled amino acids. Other labels that can be used include, but are not limited to, electron rich molecules and radioactive isotopes. Each quality control probe incorporates one or more labeled monomers during synthesis.

In a specific embodiment, the synthesis cycle in which the labeled monomer is incorporated into the quality control probe is varied with each quality control probe. Each cycle of synthesis is represented by at least one, but preferably more than one, quality control probe having a label in the monomer deposited in that synthesis cycle. Should a synthesis defect occur, no labeled monomer is incorporated and the deficiency can be detected. In a preferred aspect, each quality control probe is the same length.

In another specific embodiment, the quality control probe is made of the same number of monomers that make up the test probes on the microarray (i.e., those probes on the microarray that are not quality control probes) with one of the monomers being labeled.

In another specific embodiment, the quality control probes are varying lengths such that there is at least one, but preferably more than one, quality control probe that terminates at each cycle of synthesis. In such quality control probes, the last monomer of each of the quality control probes is a labeled monomer.

In another embodiment, quality control probes are synthesized with no predetermined binding sequence using unlabeled monomers. The signal generated relies on the monomers' intrinsic ability to generate a signal, e.g., to fluoresce. Nucleic acid quality control probes of varying lengths can be synthesized and the microarray can be scanned prior to processing by hybridization to labeled probes. The degree of fluorescence observed should correlate with the length of the quality control probes due to an increased number of monomers (nucleotides) in longer probes.

In another embodiment, a labeled dye that directly binds to the monomers of the quality control probes can be used to generate a detectable signal. For example, for a nucleic acid microarray, various fluorescent nucleic acid stains can be used such as POPO, SYBR Green I, SYBR Green II, SYTO 59, and SYTO 61 (available from Molecular Probes, Inc. in Bugene, Oreg.). After assessing the microarray synthesis efficiency, the dyes can be removed prior to incubation of the microarray with test samples.

5.3 Quality Control Probe Synthesis on Microarrays

During a step-by-step biopolymer probe synthesis onto the microarray substrate, there can be faulty monomer addition at one or more synthesis cycles of synthesis at one or more areas on the microarray. To discern if such a synthesis error occurred, quality control probes of the invention are synthesized at different places on the microarray and the signals of the different quality control probes are compared. Significant signal deviation from what is expected indicates a synthesis defect (see Section 5.4).

5.3.1 Vertical Placement

In one embodiment, quality control probes that generate a detectable signal either by binding to a predetermined binding sequence or by incorporation of labeled monomers can be displaced from each other vertically to assess the efficiency of all cycles of synthesis. In one embodiment, synthesis of the predetermined binding sequences is initiated during the step-by-step monomer addition at different cycles of synthesis. Therefore, although each predetermined binding sequence for a group of quality control probes is identical, the cycles of synthesis creating the predetermined binding sequence on the microarray are displaced from each other in a vertical fashion. In another embodiment, the cycle of synthesis in which the labeled monomer is incorporated into the quality control probe is varied such that each cycle of synthesis should have incorporated a labeled monomer in at least one quality control probe. These methods can be used to pinpoint the cycle of synthesis that was affected by faulty monomer addition.

In one embodiment, this vertical displacement is accomplished through the use of spacers. For example, by varying the number of monomers in a spacer, the synthesis cycle of the microarray at which synthesis begins of the predetermined binding sequence will also vary. Consequently, this makes each predetermined binding sequence vulnerable to defects in monomer addition occurring at different cycles in the synthesis. Should there be no synthesis defects during microarray synthesis, then the binding partner of the predetermined binding sequence should bind equally well (i.e., similarly) to the predetermined binding sequence on all of the quality control probes. In determining if the binding partner of the predetermined binding sequence on the different quality control probes are binding similarly, it must be appreciated that, when the quality control probes comprise spacers, differences in binding may be due in part to the distance the predetermined binding sequence is from the microarray (see Section 5.4). The binding differences thus expected due to the different spacer lengths are thus preferably ignored when determining whether the different quality control probes are binding "similarly".

In a specific embodiment, the quality control probes of a group all comprise identical predetermined binding sequences but differ in the overall number of monomers in the quality control probe due to a varying number of monomers comprising the spacers.

In another embodiment, this vertical displacement is accomplished by varying the synthesis cycle of the microarray at which the labeled monomer is incorporated into the quality control probe. Consequently, this makes each labeled monomer addition vulnerable to defects in monomer addition occurring at different cycles in the synthesis. Should there be no synthesis defects during microarray synthesis, then each quality control probe should have incorporated and equal number of labeled monomers and thus will give comparable signals.

In another embodiment, this vertical displacement is accomplished with a staggered start synthesis. As above, each predetermined binding sequence is displaced in its start of synthesis with respect to each other by one or more sequential cycles of monomer addition. In one embodiment, spacers are used to accomplish this displacement. In a more preferred embodiment, spacers are not used to accomplish this displacement. Rather, monomer addition is delayed at the position on the microarray to be occupied by the predetermined binding sequence until microarray synthesis has reached the cycle at which synthesis of the predetermined binding sequence is to be initiated. In this embodiment, all quality control probes comprise the same number of monomers but the synthesis using these monomers at different positions on the microarray (corresponding to the quality control probes) is separated temporally.

5.3.2 Horizontal Placement

The quality control probes of the invention can be synthesized on the microarray substrate in a number of different locations to make up a number of different patterns. These patterns can be used to identify areas of microarray synthesis defects as well to impart positional information to the microarray during processing. The number of quality control probes on a microarray should be sufficient to adequately represent the synthesis across the entire microarray. For example, the number of probes on the microarray that are quality control probes should be about 0.5% or more, 1% or more, 2% or more, 3% or ore, 5% or more, 10% or more, 20% or more, of the total probes on the microarray.

Figures 17A, 17B, 17C, 17D:
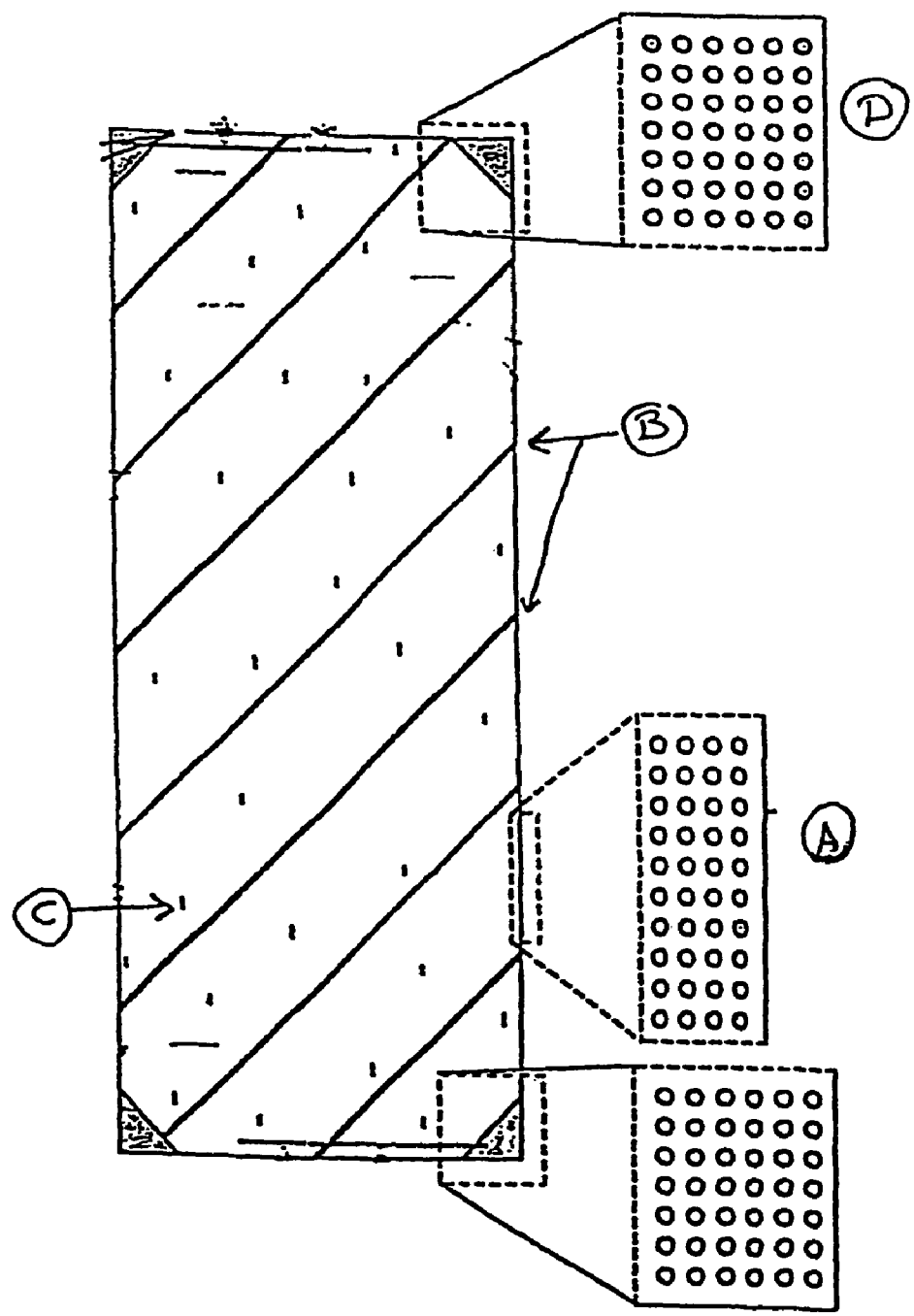

In one embodiment, one or more rows of quality control probes (called gridlines) can be synthesized at different positions throughout the microarray. Each section of the microarray can contain a gridline to ensure that all sections have been assessed for competent synthesis. In one embodiment, the integrity of biopolymer probe synthesis at the edge of the microarray can be monitored through the use of an outer (or perimeter) gridline, e.g., of 1-5 adjacent borders of quality control probes (FIG. 17A). Sections of the microarray near or at the edge can be dedicated to quality control probes such that any defect can be detected should it be present In another embodiment, the integrity of biopolymer probe synthesis in the center of the microarray can be monitored through the use of a diagonal gridline (FIG. 17B). Quality control probes can be synthesized in positions that traverse the array diagonally thus traversing representative sections of the microarray. In a preferred embodiment, gridline patterns are made up of quality control probes containing spacers.

In another embodiment clusters of quality control probes can be synthesized in sections of the microarray to assess synthesis quality. In one embodiment, quality control probes are synthesized in randomized positions throughout the middle of the array (FIG. 17C). In another embodiment, quality control probes can be synthesized at the corners of the microarray (FIG. 17D).

In another embodiment, when the microarrays are synthesized by ink jet technology, the quality control probes can be arranged on the microarray such that failures of particular nozzle(s) can be detected. A reduction in signal intensity in quality control probes that have a periodicity consistent with being printed by a particular nozzle can signify that that nozzle has been repeatedly defective. When there are N nozzles in the ink jet head, a reduction in quality control probe intensity with a periodicity of N signifies a clogged or defective nozzle (wherein N is a whole number of 1 or greater). In one embodiment, N is 20. In a further embodiment, the diagonal gridline (FIG. 17B) is used to assess nozzle clogs or defects.

In another embodiment, quality control probe patterns can be used to impart positional information about the microarray. Because the sites at which the quality control probes are synthesized during microarray synthesis are known, probes can be used to align the microarray during processing.

5.4 Detection of Defects on a Microarray

All of the quality control probes that comprise the same predetermined binding sequence should bind to the binding partner similarly. However, in many instances, the inventors have found that spacers that increase the distance of the predetermined binding S sequence from the microarray actually increase the signal intensity upon binding of a given predetermined binding sequence when compared to the signal observed from an identical predetermined binding sequence attached directly to the microarray. Without being bound by a particular mechanism, the increased signal intensity may result from the predetermined binding sequence being more accessible to its binding partner by virtue of its being further away from the microarray (e.g., by having spacers directly attached to the microarray comprising an increasing number of monomers contiguous with the predetermined binding sequence). A deviation in the amount of binding between different quality control probes and the binding partner that is greater than that expected due to differing distance of the predetermined binding sequence from the microarray may indicate a problem in microarray quality. Defects in microarray quality may be global (i.e., the defect affects the entire microarray) or localized (i.e., the defect affects one or more areas of the microarray and does not affect other areas).

In a specific embodiment, use of the quality control probe of the invention allows detection of microarray synthesis defects (e.g., a flow cell gradient where bubbles or other problems in the flow cell lead to non-uniform reagent coverage of the microarray during some of the synthesis cycles). However, other types of defects affecting microarray quality can also be detected by use of the quality control probes of the invention. Defects in the microarray can be due to occurrences other than synthesis defects. Quality control probes can be used to detect these types of defects as well. In one embodiment, microarray defects detectable by the methods of the invention occur during storage of the microarray. Suboptimal conditions (e.g., improper temperature or moisture level) can cause microarray quality to deteriorate. Other defects that are detectable by the methods of the invention include but are not limited to an abrasion that causes a localized defect on a microarray. Such an abrasion can occur during storage or processing of the microarray. A defect can occur during processing of the microarray. Such a defect can cause a non-uniformity of signal that can be detected by comparing signal intensities across the microarray. Comparison of binding intensities can be accomplished in a number of ways.

In one embodiment, a binding ratio for each set of quality control probes can be calculated. For quality control probes comprising predetermined binding sequences and not comprising spacers, signals generated during microarray processing for a particular quality control probe should equal signals generated for another different quality control probe. A ratio of the two signals should approach 1. Deviation from 1 indicates that one of the two quality control probes used in the calculation had decreased binding to its binding partner. Such would be the case if a synthesis defect caused the predetermined binding sequence in the quality control probe to be defective and thus unable to bind its binding partner at normal levels. For quality control probes comprising both predetermined binding sequence and spacers, signals generated during microarray processing for a particular quality control probe may or may not equal signals generated for another different quality control probe due to the differences in distance form the microarray. A ratio of the two signals from predetermined binding sequences that are a similar distance from the microarray (e.g., the synthesis of each predetermined binding sequence was initiated within 3 cycles of synthesis from each other) should approach 1. However, a ratio of the two signals from predetermined binding sequences that are different distances from the microarray (e.g. the synthesis of each predetermined binding sequence was initiated greater than 3 cycles of synthesis from each other) could deviate from 1. In this instance, the ratio expected can be determined using data from microarrays known to have no defects. Such microarrays can be identified, e.g., by making a plurality of arrays (preferably at least 5) and comparing the results to identity ones with no defects. Deviation from this determined expected ratio can then be used to detect defects in microarrays.

For each type of microarray (e.g., oligonucleotide, protein, etc.), the range of binding ratio values that indicates that there is no defect can be determined empirically. For example, various predetermined binding sequences known to be without defect can be bound to their binding partner and signals recorded. This can serve as the baseline values used to determine the expected binding ratios. By varying the horizontal and vertical placement of the quality control probes on the microarray, a range of acceptable ratios can be determined. Deviation from these empirically determined ratios indicates a defective microarray. In a specific embodiment, when the microarray is an oligonucleotide microarray, a binding ratio of between 0.25 and 2.25, 0.5 and 2.0, or 0.75 and 1.25 indicates no synthesis defect.

In a specific embodiment, for microarrays using quality control probes that are a mixture of those comprising predetermined binding sequences comprising one or more intentional deletions relative to a sequence that binds a binding partner used to detect the quality control probe during microarray processing and those comprising predetermined binding sequences with no intentional deletion, binding ratios can be calculated and used to assess microarray quality. Signals generated by binding of a labeled binding partner to each type of predetermined binding sequence (i.e., either with or without intentional deletions) will necessarily be different. Binding intensities determined from microarrays known to have no defects can be used to calculate expected binding ratios. Such microarrays can be identified, e.g., by making a plurality of arrays (preferably at least 5) and comparing the results to identify ones with no defects. Deviation from the expected ratio indicates a defect.

In another embodiment, comparison of binding intensities can be accomplished through a statistical analysis. The mean binding intensity for a group of quality control probes can be calculated by averaging the value of the signal (e.g., fluorescence) observed for each. The amount of signal observed for each individual quality control probe can then be compared to the mean of the group. In one embodiment, those quality control probes that are within two standard deviations from the mean indicate that there is no quality defect in the microarray, e.g., that there was no defect during their synthesis, or incurred during processing, storage, or otherwise. In a more preferred embodiment, those quality control probes that are within one standard deviation from the mean indicate that there is no defect.

In another embodiment, more than one fluorescent dye can be used to label the binding partner which binds to the predetermined binding sequence. For example, a subset of the binding partners can be labeled with Cy3 and a subset can be labeled with Cy5. A ratio of signal detected from a single quality control probe for each type of fluor used can be determined. By varying the horizontal and vertical placement of the quality control probes on the microarray, a range of acceptable ratios can be determined. Deviation from this empirically determined ratio indicates a microarray defect.

For microarrays using quality control probes without predetermined binding sequences and synthesized with labeled monomers, similar methods can be used to detect defects. Instead of the signal originating from the labeled binding partner of the predetermined binding sequence, it will come from the quality control probe itself that is attached to the microarray. Ratios and standard deviations from the mean signal can be used to assess integrity of the microarray.

For microarrays using quality control probes without predetermined binding sequences or labeled monomers, similar methods can be used to detect quality defects. In these microarrays, however, the detectable signal is proportional to the length of the quality control probe; thus, signal intensities should not be similar for each quality control probe of a differing lengths. Rather, a more intense signal is expected from longer quality control probes. Deviation from the differences expected to be seen between probes indicates a defect in the microarray.

In one embodiment, when mixtures of quality control probes are used, expected binding ratios or signal intensities can be determined empirically. Microarrays that are known to contain no defects can be used to get baseline values for predetermined binding sequence binding to its binding partner or signal intensities for each of the different types of quality control probes. Ratios can be determined from this data and used as the expected ratios. Deviation from these ratios indicates a defective microarray.

5.5 Microarray Synthesis and Processing

The probes on microarrays can be any one of a number of different biopolymers, e.g., DNAs, RNAs, peptide nucleic acids (PNAs) (see e.g., Eghohm et al., 1993, Nature 363:566-568; U.S. Pat. No. 5,539,083), or proteins. The microarrays of the invention are synthesized by a step-by-step addition of monomers onto a solid support. Each such monomer is a unit of biopolymer that is added during one synthesis cycle. In one embodiment, the unit of biopolymer added per synthesis cycle is itself composed of not more than one basic biopolymer unit (e.g., a nucleotide, amino acid, etc.). In another embodiment, the unit of biopolymer added per synthesis cycle consists of more than one basic biopolymer unit (e.g., a dinucleotide, a dipeptide, a nucleotide or amino acid covalently linked to another moiety, etc.). In another embodiment, the unit of biopolymer added per synthesis cycle varies with different synthesis cycles.

5.5.1 Nucleotide Microarrays

In a preferred embodiment in the present invention, sample processing is through hybridization on a nucleotide microarray. In a more preferred embodiment, the microarray is an oligonucleotide array. In a most preferred embodiment, the oligonucleotide array is an ink jet-synthesized oligonucleotide microarray. Preferably, the microarray contains in the range of 20 to 50,000 nucleic acid probes. The probes can be arranged in a variety of patterns. For example, the probes can be arranged in rows and columns, polygonal (e.g., hexagonal), or circular patterns, etc.

Hybridization levels are preferably measured using polynucleotide probe arrays or microarrays. On a polynucleotide array, polynucleotide probes comprising sequences of interest are immobilized to the surface of a support, e.g., a solid support. For example, the probes may comprise DNA sequences, RNA sequences, or copolymer sequences of DNA and RNA. The polynucleotide sequences of the probes may also comprise DNA and/or RNA analogues (e.g., peptide nucleic acids), or combinations thereof. For example, the polynucleotide sequences of the probe may be fill or partial sequences of genomic DNA or mRNA derived from cells, or may be cDNA or cRNA sequences derived therefrom.

The probe or probes used in the methods of the invention are preferably immobilized to a solid support or surface which may be either porous or non-porous. For example, the probes of the invention may be polynucleotide sequences which are attached to a nitrocellulose or nylon membrane or filter. Such hybridization probes are well known in the art (see, e.g., Sambrook et al., Eds., 1989, Molecular Cloning: *A Laboratory Manual*, Vols. 1-3, 2nd ed., *Cold Spring Harbor Laboratory*, Cold Spring Harbor, N.Y.). Alternatively, the solid support or surface may be a glass or plastic surface.

5.5.1.1 Hybridization Assay Using Microarrays

A microarray is an array of positionally-addressable binding (e.g., hybridization) sites on a support. Each of such binding sites comprises a plurality of polynucleotide molecules of a probe bound to the predetermined region on the support. Microarrays can be made in a number of ways, of which several are described herein below (see e.g., Meltzer, 2001, *Curr. Opin. Genet. Dev.* 11(3):258-63; Andrews et al., 2000, *Genome Res.* 10(12):2030-43; Abdellatif, 2000, Circ. Res. 86(9):919-20; Lennon, 2000, *Drug Discov. Today* 5(2): 59-66; Zweiger, 1999, *Trends Biotechnol.* 17(11):429-36). However produced, microarrays share certain characteristics. The arrays are preferably reproducible, allowing multiple copies of a given array to be produced and easily compared with each other. Preferably, the microarrays are made from materials that are stable under binding (e.g., nucleic acid hybridization) conditions. The microarrays are preferably between 1 $cm^2$ and 25 $cm^2$, preferably about 10 $cm^2$ to 15 $cm^2$. However, both larger and smaller (e.g., 0.5 $cm^2$ or less) arrays are also contemplated and may be preferable, e.g., for simultaneously evaluating a very large number of different probes.

In a particularly preferred embodiment, hybridization levels are measured to microarrays of probes consisting of a solid phase on the surface of which are immobilized a population of polynucleotides, such as a population of DNA or DNA mimics or, alternatively, a population of RNA or RNA mimics. The solid phase may be a nonporous or, optionally, a porous material such as a gel. Microarrays can be employed, e.g., for analyzing the transcriptional state of a cell such as the transcriptional states of cells exposed to graded levels of a drug of interest or to graded perturbations to a biological pathway of interest. Microarrays can be used to simultaneously screen a plurality of different probes to evaluate, e.g., each probe's sensitivity and specificity for a particular target polynucleotide.

Preferably, a given binding site or unique set of binding sites on the microarray will specifically bind (e.g., hybridize) to the product of a single gene or gene transcript from a cell or organism (e.g., to a specific mRNA or to a specific cDNA derived therefrom). However, in general, other related or similar sequences may cross hybridize to a given binding site.

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface).

Preferably, the density of probes on a microarray is about 100 different (i.e., non-identical) probes per 1 $cm^2$ or higher. More preferably, a microarray used in the methods of the invention will have at least 550 probes per 1 $cm^2$, at least 1000 probes per 1 $cm^2$, at least 1500 probes per 1 $cm^2$ or at least 2000 probes per 1 $cm^2$. In a particularly preferred embodiment, the microarray is a high density array, preferably having a density of at least about 2500 different probes per 1 $cm^2$. The microarrays used in the invention therefore preferably contain at least 2500, at least 5000, at least 10000, at least 15000, at least 20000, at least 25000, at least 50000 or at least 55000 different (i.e., non-identical) probes. A subset of these probes will correspond to spike-in tags which may have been added to the sample.

Such polynucleotides are preferably of the length of 15 to 200 bases, more preferably of the length of 20 to 100 bases, most preferably 40-60 bases. It will be understood that each probe sequence may also comprise a linker (e.g., spacer) in addition to the sequence that is complementary to its target sequence. As used herein, a linker refers to a chemical structure between the sequence that is complementary to its target sequence and the surface. The linker need not be a nucleotide sequence. For example, the linker can be composed of a nucleotide sequence, or peptide nucleic acids, hydrocarbon chains, etc.

In one embodiment, the microarray is an array (i.e., a matrix) in which each position represents a discrete binding site for a transcript encoded by a gene (e.g., for an mRNA or a cDNA derived therefrom). For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100%, or at least 50, 100, 500, 1000, or 10000 of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

Preferably, the microarrays used in the invention have binding sites (ie., probes) for sets of genes for one or more genes relevant to the action of a drug of interest or in a biological pathway of interest. As discussed above, a "gene" is identified as a portion of DNA that is transcribed by RNA polymerase, which may include a 5' untranslated region (UTR), introns, exons and a 3' UTR The number of genes in a genome can be estimated from the number of MRNA molecules expressed by the cell or organism, or by extrapolation of a well characterized portion of the genome. When the genome of the organism of interest has been sequenced, the number of open reading frames (ORFs) can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546-567). In contrast, the human genome is estimated to contain approximately 30000 to 130000 genes (see Crollius et al., 2000, *Nature Genetics* 25:235-238; Ewing et al., 2000, *Nature Genetics* 25:232-234). Genome sequences for other organisms, including but not limited to *Drosophila, C. elegans,* plants, e.g., rice and *Arabidopsis,* and mammals, e.g., mouse and human, are also completed or nearly completed. Thus, in preferred embodiments of the invention, array set comprising probes for all genes in the genome of an organism is provided.

It will be appreciated that when a sample of target nucleic acid molecules, e.g., cDNA complementary to the RNA of a cell is made and hybridized to a microarray under suitable hybridization conditions, the level of hybridization to the site in the array will reflect the prevalence of the corresponding complementary sequences in the sample. For example, when detectably labeled (e.g., with a fluorophore) cDNA is hybridized to a microarray, the site on the array corresponding to a nucleotide sequence that is not in the sample will have little or no signal (e.g., fluorescent signal), and a nucleotide sequence that is prevalent in the sample will have a relatively strong signal. The relative abundance of different nucleotide sequences in a sample may be determined by the signal strength pattern of probes on a microarray.

Nucleic acids from samples from two different cells subjected to two different conditions can be hybridized to the binding sites of the microarray using a two-color protocol. In the case of drug responses, one cell sample is exposed to a drug and another cell sample of the same type is not exposed to the drug. The cDNA derived from each of the two cell types is differently labeled (e.g., with Cy3 and Cy5) so that they can be distinguished. In one embodiment, for example, cDNA from a cell treated with a drug (or having a mutation or a disease, etc.) is synthesized using a fluorescein-labeled dNTP, and cDNA from a second cell, not drug-exposed, is synthesized using a rhodamine-labeled dNTP. When the two cDNA molecules are mixed and hybridized to the microarray, the relative intensity of signal from each cDNA set is determined for each site on the array, and any relative difference in abundance of a particular gene detected.

In the example described above, the nucleic acid from the drug-treated cell will fluoresce green when the fluorophore is stimulated and the nucleic acid from the untreated cell will fluoresce red. As a result, when the drug treatment has no effect, either directly or indirectly, on the transcription of a particular gene in a cell, the expression patterns will be indistinguishable in both cells and, upon reverse transcription, red-labeled and green-labeled nucleic acids will be equally prevalent. When hybridized to the microarray, the binding site(s) for that species of nucleic acid will emit wavelengths characteristic of both fluorophores. In contrast, when the drug-exposed cell is treated with a drug that, directly or indirectly, change the transcription of a particular gene in the cell, the expression pattern as represented by ratio of green to red fluorescence for each binding site will change. When the drug increases the prevalence of an mRNA, the ratios for each binding site of the mRNA will increase, whereas when the drug decreases the prevalence of an mRNA, the ratio for each for each binding site in the mRNA will decrease.

The use of a two-color fluorescence labeling and detection scheme to define alterations in gene expression has been described in connection with detection of mRNA molecules, e.g., in Shena et al., 1995, Quantitative monitoring of gene expression patterns with a complementary DNA microarray, Science 270:467-470. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'-carboxy-fluorescein (FMA), 2',7'-dimethoxy4',5'-dichloro-6-carboxy-fluorescein (JOE), N,N,N',N'-tetramethyl-6-carboxy-rhodamine (TAMRA), 6'carboxy-X-rhodamine ROX), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

5.5.1.2 Preparing Probes for Microarrays

As noted above, the probe to which a particular polynucleotide molecule specifically hybridizes is a complementary polynucleotide sequence. Typically each probe on the microarray will be between 20 bases and 600 bases, and usually between 30 and 200 bases in length.

The means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 600 bases in length, more typically between about 20 and about 100 bases, most preferably between about 40 and about 70 bases in length.

The probes on the microarrays are macromolecules attached to the solid support of a microarray. In the present invention, the probes are preferably nucleic acid sequences (or fragments thereof).

5.5.1.3 Attaching Probes to the Solid Surface

Methods of the invention utilize polynucleotide probes synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A method for making microarrays is by making high-density oligonucleotide arrays. There are a variety of techniques known for producing arrays containing thousands of oligonucleotides complementary to defined sequences, at defined locations on a surface. For example, photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature BioTechnology 14:1675; U.S. Pat. Nos. 5,489,678; 5,578,832; 5,556,752; 5,510,270; 6,197,506; and 6,346,413) or other methods for rapid synthesis and deposition of defined oligonucleotides (Blanchard et al., Biosensors & Bioelectronics 11:687-690) may be used.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed, Plenum Press, New York at pages 111-123; Hughes et al., 2001, *Nature BioTechnology* 19:342-347; and U.S. Pat. No. 6,028,189 to Blanchard. Specifically, the oligonucleotide probes in such microarrays are preferably synthesized in arrays, e.g., on a glass slide, by serially depositing individual nucleotide bases in microdroplets of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are attached to the surface covalently at the 3' end of the polynucleotide.

When these methods are used, oligonucleotides (e.g., 60-mers) of known sequence are synthesized directly on a surface such as a derivatized glass slide. The array produced can be redundant, with several oligonucleotide molecules per gene.

5.5.1.4 Target Polynucleotide Molecules

Target polynucleotides are the polynucleotides of the biological samples that are being processed on the microarray. Target polynucleotides can be RNA molecules such as, but by no means limited to messenger RNA (mRNA) molecules, ribosomal RNA (rRNA) molecules, cRNA molecules (i.e., RNA molecules prepared from cDNA molecules that are transcribed in vitro) and fragments thereof. Additionally, target polynucleotides may also be, but are not limited to, DNA molecules such as genomic DNA molecules, cDNA molecules, and fragments thereof including oligonucleotides, ESTs, STSs, etc. In specific embodiments, the sample comprises more than 1000, 5000, 10000, 50000, 100000, 250000, or 1000000 nucleic acid molecules of different nucleotide sequences.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)+ messenger RNA, fraction thereof) and messenger RNA is purified from the total extracted RNA. Methods for preparing total and poly(A)+ RNA are well known in the art, and are described generally, e.g. in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, total RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from cDNA prepared from purified mRNA or from total RNA extracted from cells. As used herein, cRNA can either be complementary to (anti-sense) or of the same sequence (sense) as the sample RNA. The extracted RNA molecules are amplified using a process in which double-stranded cDNA molecules are synthesized from the sample RNA molecules using primers linked to an RNA polymerase promoter. As a result, RNA polymerase promoters can be incorporated into either or both strands of the cDNA. Using the RNA polymerase promoter that is on the first strand of the cDNA molecule, cRNA can be synthesized that is the same sequence as the sample RNA. To synthesize cRNA complementary to the sample RNA, transcription can be initiated from the RNA polymerase promoter that is on the second strand of the double-stranded cDNA molecule using an RNA polymerase (see, e.g., U.S. Pat. Nos. 5,891,636, 5,716,785; 5,545,522 and 6,132,997; see also, U.S. Pat. No. 6,271,002 and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleotides are short and/or fragmented polynucleotide molecules which are representative of the original nucleic acid population of the cell. In one embodiment, total RNA is used as input for cRNA synthesis. An oligo-dT primer containing a T7 RNA polymerase promoter sequence can be used to prime first strand cDNA synthesis. When second strand synthesis is desired, random hexamers can be used to prime second strand cDNA synthesis by a reverse transcriptase. This reaction yields a double-stranded cDNA that contains the T7 RNA polymerase promoter at the 3' end. The double-stranded cDNA can then be transcribed into cRNA by T7 RNA polymerase.

The target polynucleotides to be analyzed are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}P$, $^{35}S$, $^{14}C$, $^{15}N$ and $^{125}I$. Fluorescent molecules suitable for the present invention include, but are not limited to, fluorescein and its derivatives, rhodamine and its derivatives, texas red, 5'carboxy-fluorescein (FMA), 2',7'-dimethoxy-4',5'-dichloro-6-carboxy-fluorescein (JOE), N,N,N',N'-tetramethyl-6-carboxy-rhodamine (TAMRA), 6'carboxy-X-rhodamine (ROX), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and imminobiotin. Compounds suitable for use as a second group include, but are not limited to, avidin and streptavidin.

The binding partners of the predetermined binding sequence of the quality control probes can be added to the target molecules prior to contact with the microarray. In one embodiment, the binding partners are added to the target molecules during target molecule processing. In a more preferred embodiment, the binding partners are added tot he target molecules immediately prior to contacting the microarray.

5.5.1.5 Hybridization to Microarrays

As described supra, nucleic acid hybridization and wash conditions are chosen so that the polynucleotide molecules to be analyzed (or target polynucleotide molecules) specifically bind or specifically hybridize to the complementary polynucleotide sequences of the array, preferably to one or more specific array sites, wherein its complementary sequence is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, Current Protocols in Molecular Biology, Greene Publishing and Wiley-Interscience, New York. For example, when cDNA microarrays are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Hughes et al., 2001, Nature BioTechnology 19:342-347). Useful hybridization conditions are also provided in, e.g., Tijessen, 1993, Hybridization With Nucleic Acid Probes, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1M NaCl, 50 mM MES buffer (pH 6.5), 0.5% sodium Sarcosine and 30% formamide.

5.5.1.6 Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to a particular gene will reflect the prevalence in the cell of mRNA or mRNA molecules containing the transcript from that gene. For example, when detectably labeled (e.g., with a fluorophore) cDNA complementary to the total cellular mRNA is hybridized to a microarray, the site on the array corresponding to a gene (i.e., capable of specifically binding the product or products of the gene expressing) that is not transcribed in the cell will have little or no signal (e.g., fluorescent signal), and a gene for which the encoded mRNA expressing the transcript is prevalent will have a relatively strong signal.

In preferred embodiments, target sequences, e.g., cDNA molecules or cRNA molecules, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or otherwise perturbed) is synthesized using a fluorescein-labeled dNTP, and cDNA from a second cell, not drug-exposed, is synthesized using a rhodamine-labeled dNTP. When the two cDNA molecules are mixed and hybridized to the microarray, the relative intensity of signal from each cDNA set is determined for each site on the array, and any relative difference in abundance of a particular transcript detected.

In the example described above in the previous paragraph, the cDNA from the drug-treated (or otherwise perturbed) cell will fluoresce green when the fluorophore is stimulated and the cDNA from the untreated cell will fluoresce red. As a result, when the drug treatment has no effect, either directly or indirectly, on the transcription of a particular gene in a cell, the expression pattern will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription splicing of a particular gene in the cell, the expression pattern as represented by ratio of green to red fluorescence for each transcript binding site will change. When the drug increases the prevalence of an mRNA, the ratios for each transcript fragment expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNA molecules, e.g., in Shena et al., 1995, Quantitative monitoring of gene expression patterns with a complementary DNA microarray, Science 270:467-470. An advantage of using target sequences, e.g., cDNA molecules or cRNA molecules, labeled with two different fluorophores is that a direct and internally controlled comparison of the mRNA expression levels corresponding to each arrayed gene in two cell states can be made, and variations due to minor differences in experimental conditions (e.g. hybridization conditions) will not affect subsequent analyses. However, it will be recognized that it is also possible to use cDNA from a single cell and compare, for example, the absolute amount of a particular exon in, e.g., a drug-treated or otherwise perturbed cell and an untreated cell.

In other preferred embodiments, single channel detection methods, e.g. using one-color fluorescence labeling, are used (see U.S. patent application Ser. No. 09/781,814, filed on Feb. 12, 2001). In this embodiment, arrays comprising reverse-complement (RC) probes are designed and produced. Because a reverse complement of a DNA sequence has sequence complexity that is equivalent to the corresponding forward-strand (FS) probe that is complementary to a target sequence with respect to a variety of measures (e.g., measures such as GC content and GC trend are invariant under the reverse complement), a RC probe is used to as a control probe for determination of level of non-specific cross hybridization to the corresponding FS probe. The significance of the FS probe intensity of a target sequence is determined by comparing the raw intensity measurement for the FS probe and the corresponding raw intensity measurement for the RC probe in conjunction with the respective measurement errors. In a preferred embodiment, a transcript is called present if the intensity difference between the FS probe and the corresponding RC probe is significant. More preferably, a transcript is called present if the FS probe intensity is also significantly above background level. Single channel detection methods can be used in conjunction with multi-color labeling. In one embodiment, a plurality of different samples, each labeled with a different color, is hybridized to an array. Differences between FS and RC probes for each color are used to determine the level of hybridization of the corresponding sample.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Res. 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, Genome Res. 6:639-645. Alternatively, the fiber-optic bundle described by Ferguson et al., 1996, Nature BioTechnology 14:1681-1684, may be used to monitor mRNA abundance levels at a large number of sites simultaneously.

Signals are recorded and, in a preferred embodiment, analyzed by computer, e.g., using a 12 bit or 16 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for cross talk (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

The relative abundance of an mRNA in two cells or cell lines is preferably scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is preferably scored as a perturbation.

It is, however, also advantageous to determine the magnitude of the relative difference in abundances for an mRNA expressed in an mRNA in two cells or in two cell lines. This can be carried out, as noted above, by calculating the ratio of the emission of the two fluorophores used for differential labeling, or by analogous methods that will be readily apparent to those of skill in the art 5.5.2 Protein Microarrays In an embodiment-in-the-present invention, the microarray is a protein microarray. As a result, the quality control probe in this embodiment is a polypeptide or peptide. Protein quality control probes preferably have a corresponding binding partner available such that contacting the probe with said binding partner can allow for specific and quantifiable binding.

On a protein microarray, protein probes possessing the ability to bind proteins of interest are immobilized to the surface of a substrate, e.g., a solid support (see e.g., Goffeau et al., 1996, Science 274:546-567; Aebersold et al., 1999, Nature BioTechnology 10:994-999; Haab et al., 2001, Genome Biology 2:RESEARCH0004.1-RESEARCH0004.13; U.S. Pat. No. 6,346,413). For example, polypeptide probes may be prepared using standard solid-phase techniques for the synthesis of peptides. As is generally known, polypeptides can be prepared using commercially available equipment and reagents following the manufacturers' instructions for blocking interfering groups, protecting the amino acid to be reacted, coupling, deprotection, and capping of unreacted residues. The protein probes may contain non-peptide linkages and/or modified or non-naturally occurring amino acids, e.g., D-amino acids, phosphorous analogs of amino acids, such as $\alpha$-amino phosphoric acids and $\beta$-amino phosphoric acids.

The probes used in the methods of the invention are preferably synthesized on a solid support or surface which may be either porous or non-porous. For example, the probes of the invention may be polypeptide sequences which are attached to a nitrocellulose or nylon membrane or filter. Alternatively, the solid support or surface may be a glass or plastic surface.

Proteins can be synthesized on a positionally addressable array with a plurality of proteins attached to a substrate, with each protein being at a different position on the solid support. Preferably, the plurality of proteins comprises at least 10, 50, 100, 250, 500, 1000, 1500, 2000, 2500, 3000, 4000, 5000, 6000, 7000, 8000, 9000, 10000, 50000, or 100000 different polypeptides expressed in a single biological sample, plus the quality control probes. Protein probes are synthesized onto the substrate in a step-by-step synthesis using amino acid monomers.

In one embodiment, the quality control probe is an antibody or fragment thereof. In another embodiment, the binding partner of the quality control probe is an antibody or fragment thereof. In a preferred embodiment, the antibody is a monoclonal antibody or fragment (e.g., Fab fragment) thereof (see, e.g., Zhu et al., 2001, Science 293:2101-2105; MacBeath et al., 2000, Science 289:1760-63; de Wildt et al., 2000, Nature BioTechnology 18:989-994).

It will be appreciated that when a sample of protein is bound to a protein microarray under suitable conditions, the level of binding to a particular site in the array will reflect the prevalence of the corresponding binding partner in the sample. The level of binding between polypeptide quality control probe on the microarray and its protein binding partner is preferably indicated by signaling compounds. For example, when a protein sample is bound to a protein microarray, the site on the array corresponding to a polypeptide probe with a corresponding binding partner not in the sample will have little or no signal, and a polypeptide probe with a corresponding binding partner that is prevalent in the sample will have a relatively strong signal. The relative abundance of different proteins in a sample may be determined by the signal strength pattern of probes on a microarray. In one embodiment, one or more signal compounds (e.g., fluorescent dyes) are directly attached to the protein binding partner of the quality control probe. In another embodiment, one or more signal compounds are attached to the protein binding partner of the quality control probe indirectly (e.g., through the use of a fluorescently labeled antibodies).

5.6 Implementation Systems and Methods

The analytical methods of the present invention can preferably be implemented using a computer system, such as the computer system described in this section, according to the following programs and methods. Such a computer system can also preferably store and manipulate a database of the present invention which comprises a compendium of positional information pertaining to the location of quality control probes on the microarray as well as in which sequential cycles of synthesis they were synthesized (i.e., the vertical placement in the microarray) and which can be used by a computer system in implementing the analytical methods of this invention. Accordingly, such computer systems are also considered part of the present invention. In a specific embodiment, the quality control positional information is stored in digital form in a database.

In a specific embodiment, the computer system comprises one or more processing units and one or more memory units connected to said one or more processor units. Said one or more memory units contain one or more programs which cause said one or more processor units to execute steps of comparing the binding to their binding partner of two or more of the quality control probes on an array of the invention. The result is output, preferably as a binding ratio of the quality control probes. In a specific embodiment, the computer programs cause said one or more processors to execute steps of (a) receiving a first data structure comprising the binding intensity of the quality control probes on the processed microarray; and (b) comparing said first data structure to a plurality of data structures in a database, each data structure comprising positional information regarding the quality control probes associated with said microarray, to identify the relevant positions on the said microarray to compare to assess synthesis integrity; and (c) comparing the binding of two or more quality control probes.

In a specific embodiment, the computer system comprises a program that causes the processor to compare the appropriate quality control probe binding intensities and thereby determine if the microarray was synthesized correctly.

In another embodiment, the computer system performs one or more aspects of the sample quality control. For example, the computer can read the microarray's quality control probe intensities directly from the raw data represented in a TIFF file of the scanned microarray image and compare the appropriate intensities, and determine if the synthesis of the array is defective, thus resulting in suspect data. If a synthesis defect is identified, the computer could generate a non-conformance report and refrain from automatically adding the suspect data to the database containing microarray possessing data until the quality control issues are further addressed. In one embodiment, the computer would generate a non-conformance report if the binding ratio of the quality control probes is not between 0.5 and 2.0.

An exemplary computer system suitable for implementing the analytic methods of this invention preferably comprises internal components being linked to external components. The internal components of this computer system include a processor element interconnected with a main memory. For example, the computer system can be an Intel Pentium®-based processor of 200 MHZ or greater clock rate and with 32 MB or more main memory. In a preferred embodiment, the computer system is a cluster of a plurality of computers comprising a head "node" and eight sibling "nodes", with each node having a central processing unit (CPU). In addition, the cluster also comprises at least 128 MB of random access memory (RAM) on the head node and at least 256 MB of RAM on each of the eight sibling nodes. Therefore, the computer systems of the present invention are not limited to those consisting of a single memory unit or a single processor unit.

The external components can include a mass storage. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device, which is most typically a monitor and a keyboard together with a graphical input device such as a "mouse". The computer system is also typically linked to a network link which can be, e.g., part of a local area network (LAN) to other, local computer systems and/or part of a wide area network (WAN), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components. The software components comprise both software components that are standard in the art and components that are special to the present invention. These software components are typically stored on mass storage such as the hard drive, but can be stored on other computer readable media as well including, for example, one or more floppy disks, one or more CD-ROMs, one or more DVDs or one or more DATs. The software component represents an operating system which is responsible for managing the computer system and its network interconnections. The operating system can be, for example, of the Microsoft Windows™ family such as Windows 95, Window 98, Windows NT or Windows2000. Alternatively, the operating software can be a Macintosh operating system, a UNIX operating system or the LNX operating system. The software components comprise common languages and functions that are preferably present in the system to assist programs implementing methods specific to the present invention. Languages that can be used to program the analytic methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematical from Wolfram Research (Champaign, Ill.) or S-Plus from MathSoft (Seattle, Wash.).

The software component comprises analytic methods of the present invention, preferably programmed in a procedural language or symbolic package. For example, the software component preferably includes programs that cause the processor to implement steps of accepting a plurality of positional data for each quality control probe on each microarray and storing the data in the memory. For example, the computer system can accept data manually entered by a user (e.g., by means of the user interface). Alternatively, however, the programs cause the computer system to retrieve quality control probe information from a database. Such a database can be stored on a mass storage (e.g., a hard drive) or other computer readable medium and loaded into the memory of the computer, or the database can be accessed by the computer system by means of the network.

In one embodiment, the computer readable medium contains an encoded data structure comprising:

(a) a digital representation of the position of the quality control probes on the microarray; and (b) a digital representation of the cycles of synthesis at which each quality control probe was synthesized.

In another embodiment, control microarrays with intentional defects can be processed and signal intensity patterns and ratios can be stored. The present invention also encompasses a process by which the signal intensity(ies) and/or resulting ratios from the sample microarray are compared to the database containing a compendium of known errors. Should a match be found in the database, the defect in the sample microarray can be determined.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

The following examples are presented by way of illustration of the present invention, and are not intended to limit the present invention in any way.

6. EXAMPLE 1

Quality Control Using Quality Control Probes

6.1 Demonstration of Synthesis Error

The inkjet writer uses two inkjet heads for distributing phosphoramidites or activator onto the glass substrate of the array. Each head contains three sets of 20 nozzles with each 20-nozzle set dedicated for depositing either a single phosphoramidite or the activator. The 20 nozzles in a set are arranged in two interlaced columns of ten (see FIG. 1). This pattern allows for the deposition of 20 rows of bases per pass of the inkjet heads, with each nozzle being responsible for a single row. Because each nozzle is responsible for a particular row, any clog or other nozzle malfunction can result in all or a portion of rows being deleted or synthesized inefficiently (detected by a reduction of intensity in the affected quality control probes) with a 20 row periodicity. FIG. 1 shows a 25,000 oligonucleotide array synthesized with three clogged nozzles (i.e., nozzles 4, 15, and 20).

6.2 Synthesis Failure Detection

Figure 2A:
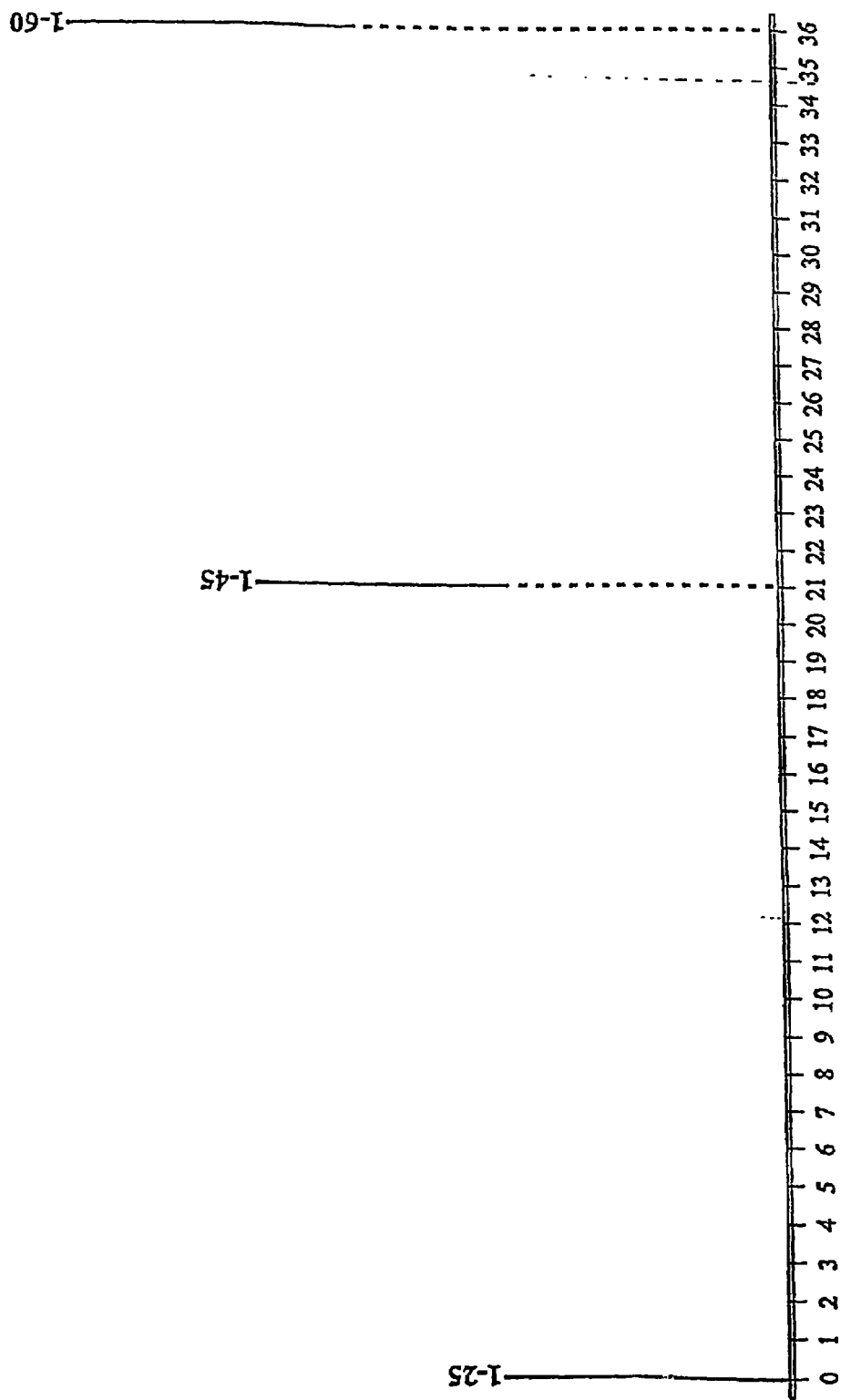

Silted quality control probes are depicted schematically in FIG. 2A. A 25 nucleotide predetermined binding sequence (depicted by a solid line) is synthesized either directly on the microarray (so that the sequence is made at synthesis cycles 1-25) or on spacers (depicted by a dashed line). The spacer are shown to be either 20 nucleotides long (so that the sequence is made at synthesis cycles 21-45) or 35 nucleotides long (so that the sequence is made at synthesis cycles 36-60). Should there be no synthesis defects during oligonucleotide microarray synthesis, then the reverse complement of the predetermined binding sequence should hybridize equally well to the predetermined binding sequence on all of the quality control probes and give comparable signals.

Figure 2B:
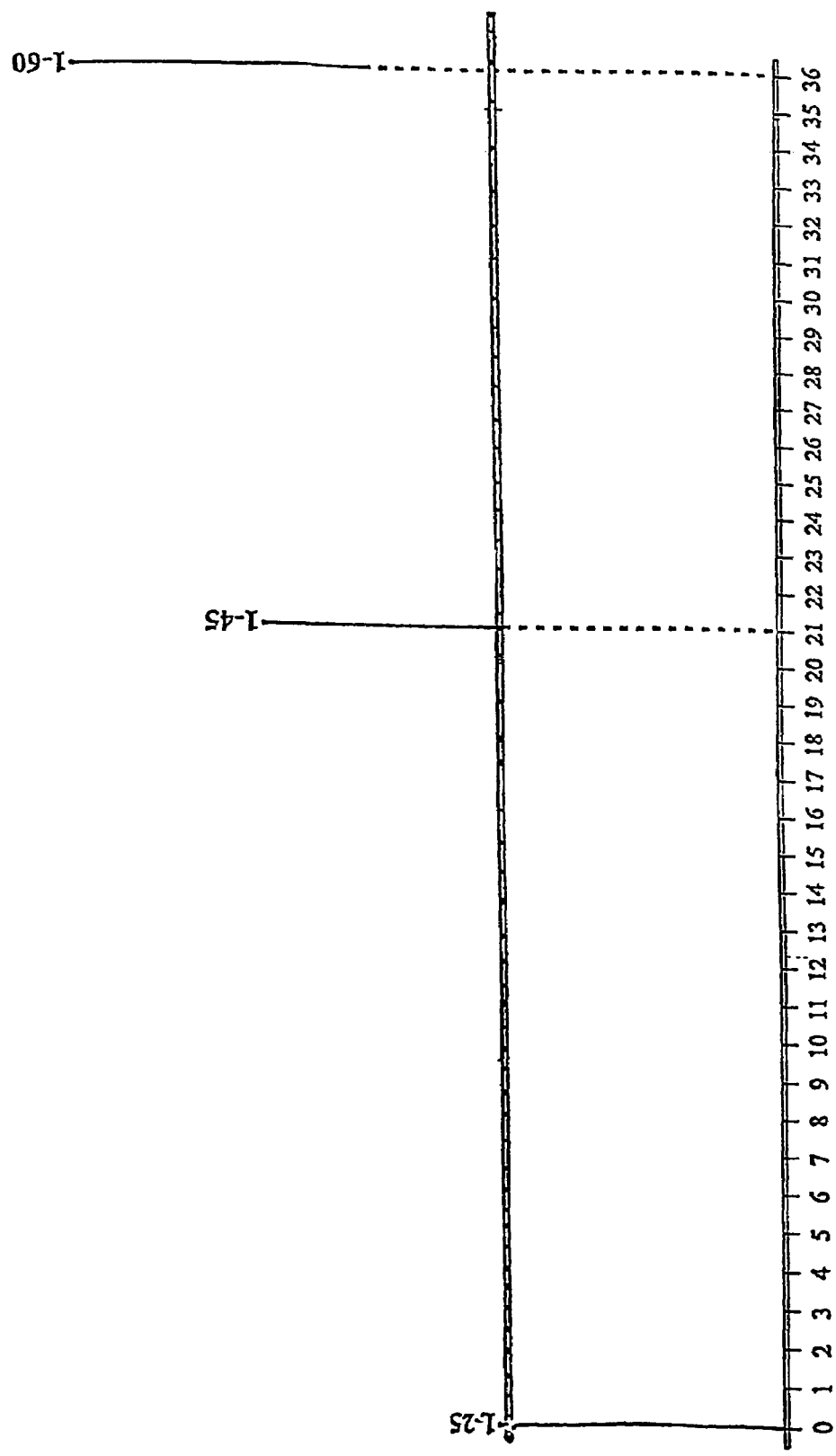

FIG. 2B schematically depicts a synthesis defect in synthesis cycle 24 of the oligonucleotide microarray (depicted by the striped bar). Because this affects the sequence of the predetermined binding sequence when it is either on no spacer or on a 20 nucleotide spacer, hybridization to its reverse complement will be decreased when compared to the level of binding that is observed with no synthesis error. The predetermined binding sequence on a 35 nucleotide spacer is unaffected; however, thus it should hybridize to its reverse complement to the same degree as when no synthesis error was present.

A quality control probe having the sequence of SEQ ID NO:1 was synthesized on an ink jet oligonucleotide microarray with either no spacer (with total length of 25 nucleotides), on a 20 oligonucleotide spacer (with total length of 45 nucleotides), or on a 35 oligonucleotide spacer (with total length of 60 nucleotides).

5' ATCATCGTAGCTGGTCAGTGTATCC 3' (SEQ ID NO:1)

Figure 4A:
Figure 4B:
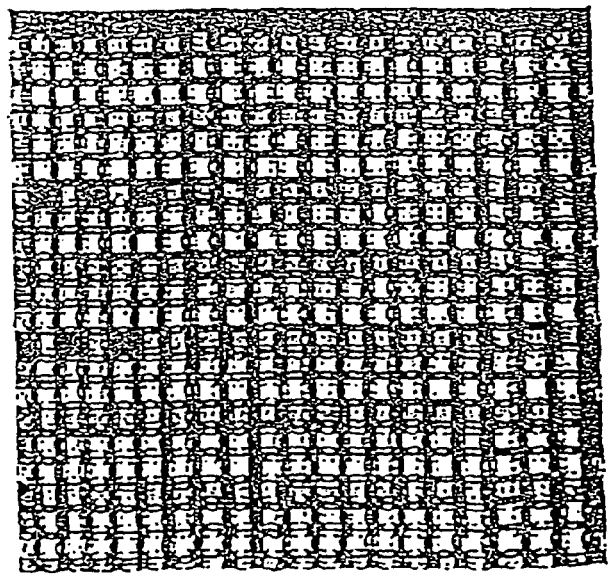
Figures 5A, 5B:
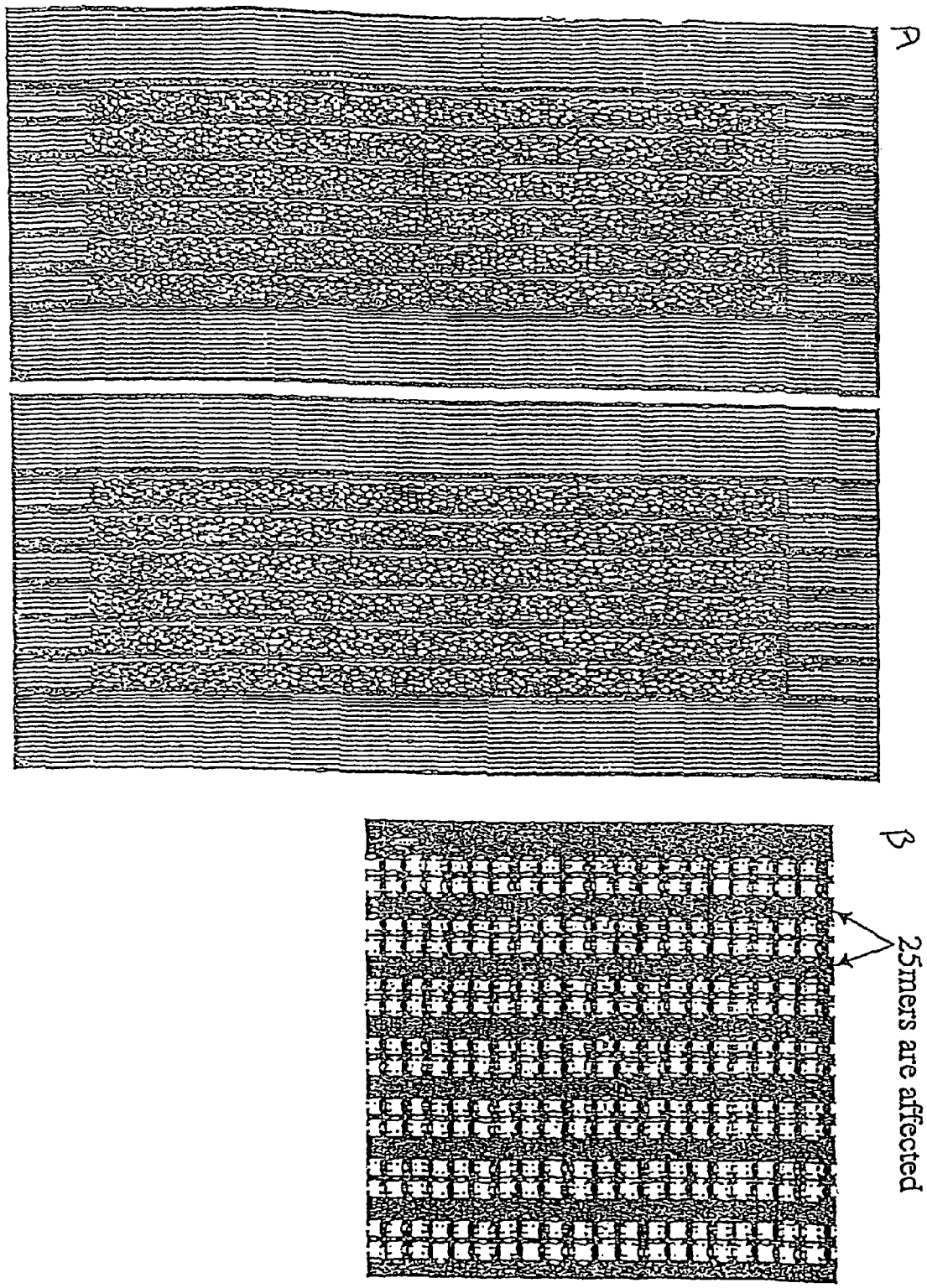
Figure 6A:
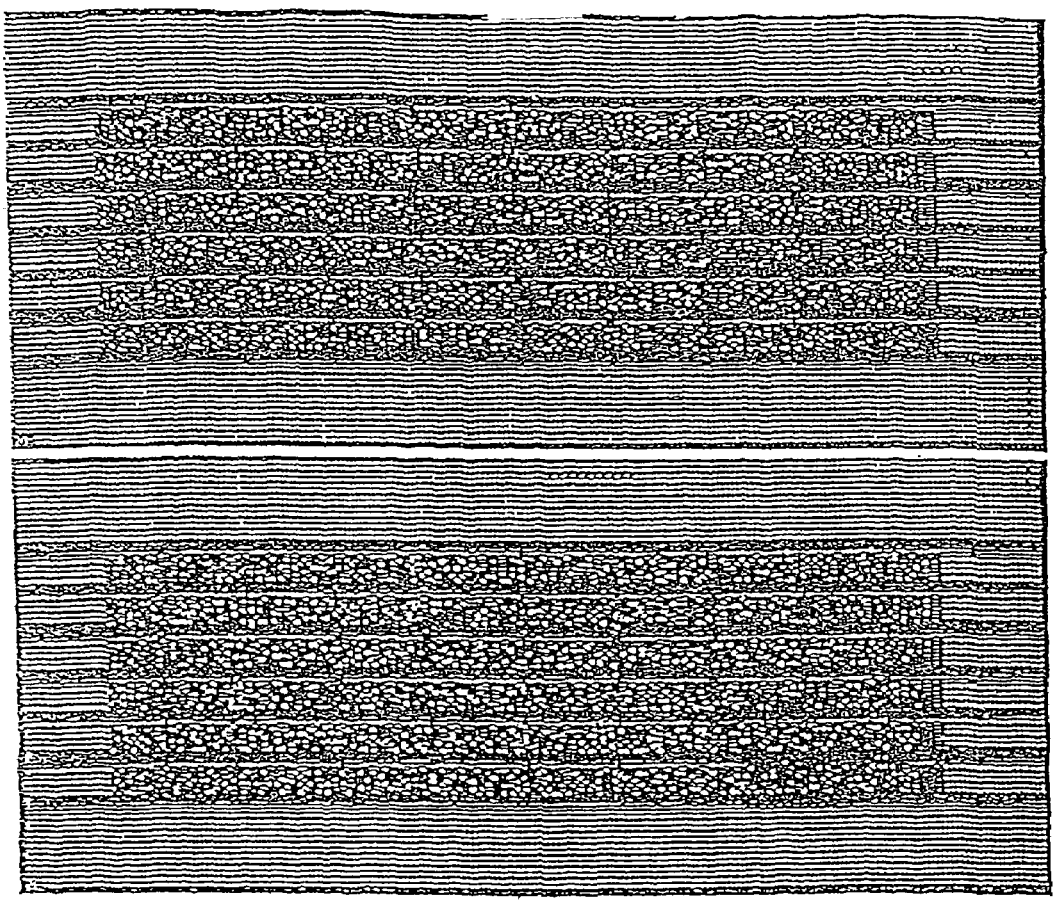
Figure 6B:
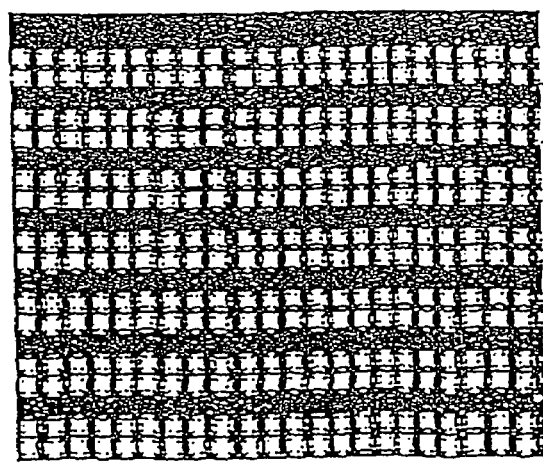
Figures 8A, 8B:
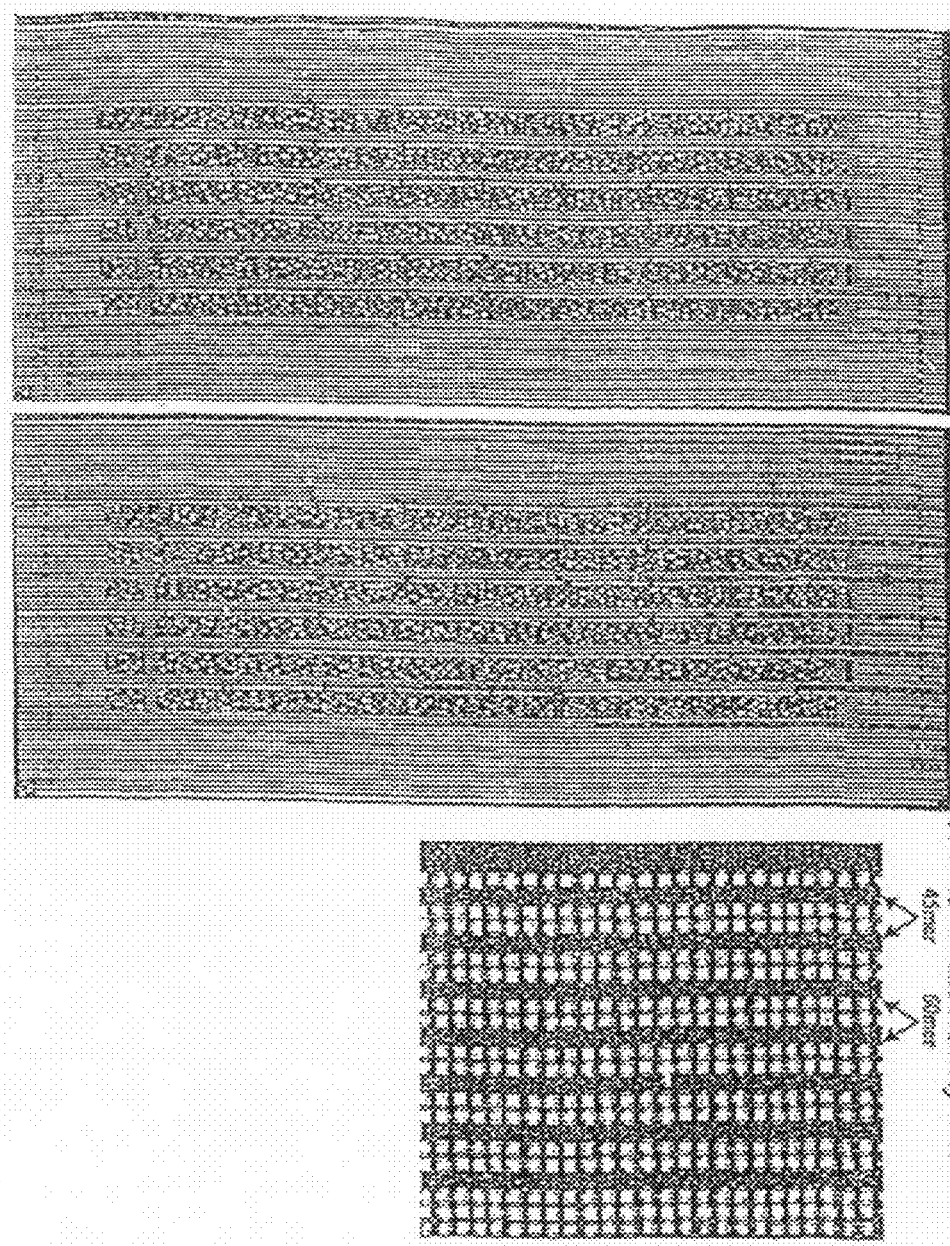

The fluorescently labeled reverse complement of SEQ ID NO:1 was used to hybridize to the oligonucleotide microarray. When there were no synthesis defects during oligonucleotide microarray synthesis, all of the quality control probes hybridized to their reverse complement equally well (FIG. 4). This was shown by the comparable levels of hybridization to a fluorescently labeled reverse complementary nucleotide after microarray processing (see FIGS. 4A-4B). Data quantifying fluorescent intensity for each quality control probe was done in duplicate on two microarrays and is given in Table 1. Ratios of average fluorescent intensity of the 25 mer to the average fluorescent intensity of the 45 mer or 60 mer approach 1 and indicates that all bound to their reverse complement comparably.

Figure 9A:
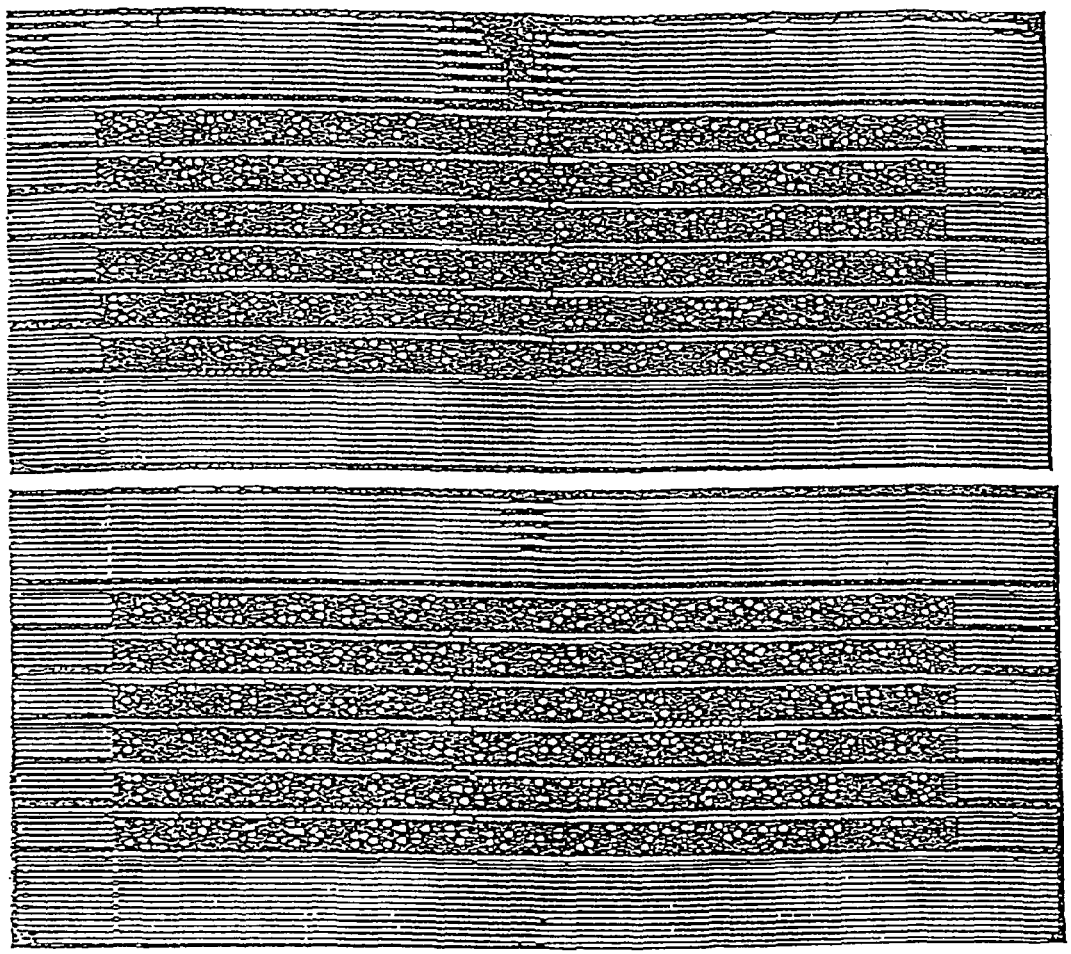
Figure 9B:
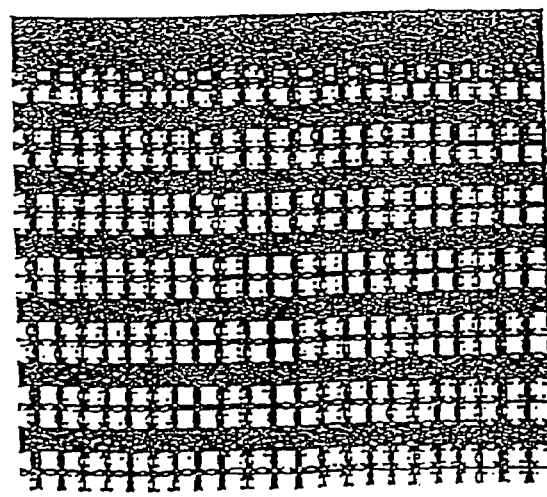

Similar experiments were conducted with various synthesis cycles being defective during microarray synthesis in order to ascertain the sensitivity of the quality control probes. When the first (FIG. 5) or first and second (FIG. 6) synthesis cycles were skipped during synthesis, only the 25 mer hybridization to its complementary fluorescently labeled oligonucleotide was affected (FIGS. 5A-5B and 6A-6B). Both ratios in Table 1 show a decrease with respect to ratios seen when no synthesis cycles are skipped. When the thirty sixth (FIG. 7) or thirty fourth and thirty fifth (FIG. 8) synthesis cycles were skipped, both of the 45 mer and 60 mer hybridization to their complementary fluorescently labeled oligonucleotides were affected (FIGS. 7A-7B and 8A-8B). Both ratios in Table 1 show an increase with respect to ratios seen when no synthesis cycles are skipped. When there was inefficient synthesis in the first twenty two synthesis cycles (FIG. 9), only the 25 mer hybridization to its complementary fluorescently labeled oligonucleotide was severely affected (FIG. 9A-9B). Both ratios in Table 1 show a decrease with respect to ratios seen when no synthesis cycles are skipped or inefficient.

TABLE 1

| synthesis cycles affected | | array 1 | array 2 | average | ratio of 25 mer/ 45 mer | ratio of 25 mer/ 60 mer |
|---|---|---|---|---|---|---|
| None | 25 mer | 0.0628 | 0.0495 | 0.0562 | 1.28 | 1.03 |
|  | 45 mer | 0.0413 | 0.0399 | 0.0406 |  |  |
|  | 60 mer | 0.535 | 0.0555 | 0.0545 |  |  |
| 1 | 25 mer | 0.0133 | 0.0149 | 0.0141 | 0.28 | 0.20 |
|  | 45 mer | 0.0461 | 0.0536 | 0.0499 |  |  |
|  | 60 mer | 0.0656 | 0.0770 | 0.0713 |  |  |
| 1-2 | 25 mer | 0.0056 | 0.0044 | 0.005 | 0.10 | 0.07 |
|  | 45 mer | 0.0532 | 0.0442 | 0.0476 |  |  |
|  | 60 mer | 0.0793 | 0.0675 | 0.0734 |  |  |
| 36 | 25 mer | 0.0692 | 0.0730 | 0.0711 | 5.47 | 2.30 |
|  | 45 mer | 0.0120 | 0.0140 | 0.013 |  |  |
|  | 60 mer | 0.0278 | 0.0339 | 0.0309 |  |  |
| 34-35 | 25 mer | 0.1028 | 0.0644 | 0.0836 | 42.0 | 1.87 |
|  | 45 mer | 0.0020 | 0.0019 | 0.0195 |  |  |
|  | 60 mer | 0.0471 | 0.0427 | 0.0449 |  |  |
| 1-22 | 25 mer | 0.0024 | 0.0020 | 0.0022 | 0.008 | 0.008 |
|  | 45 mer | 0.2165 | 0.3682 | 0.2924 |  |  |
|  | 60 mer | 0.2640 | 0.2962 | 0.2801 |  |  |

7. EXAMPLE 2

Quality Control Using Quality Control Probes with No Spacers

7.1 Synthesis Failure Detection

Figure 3A:
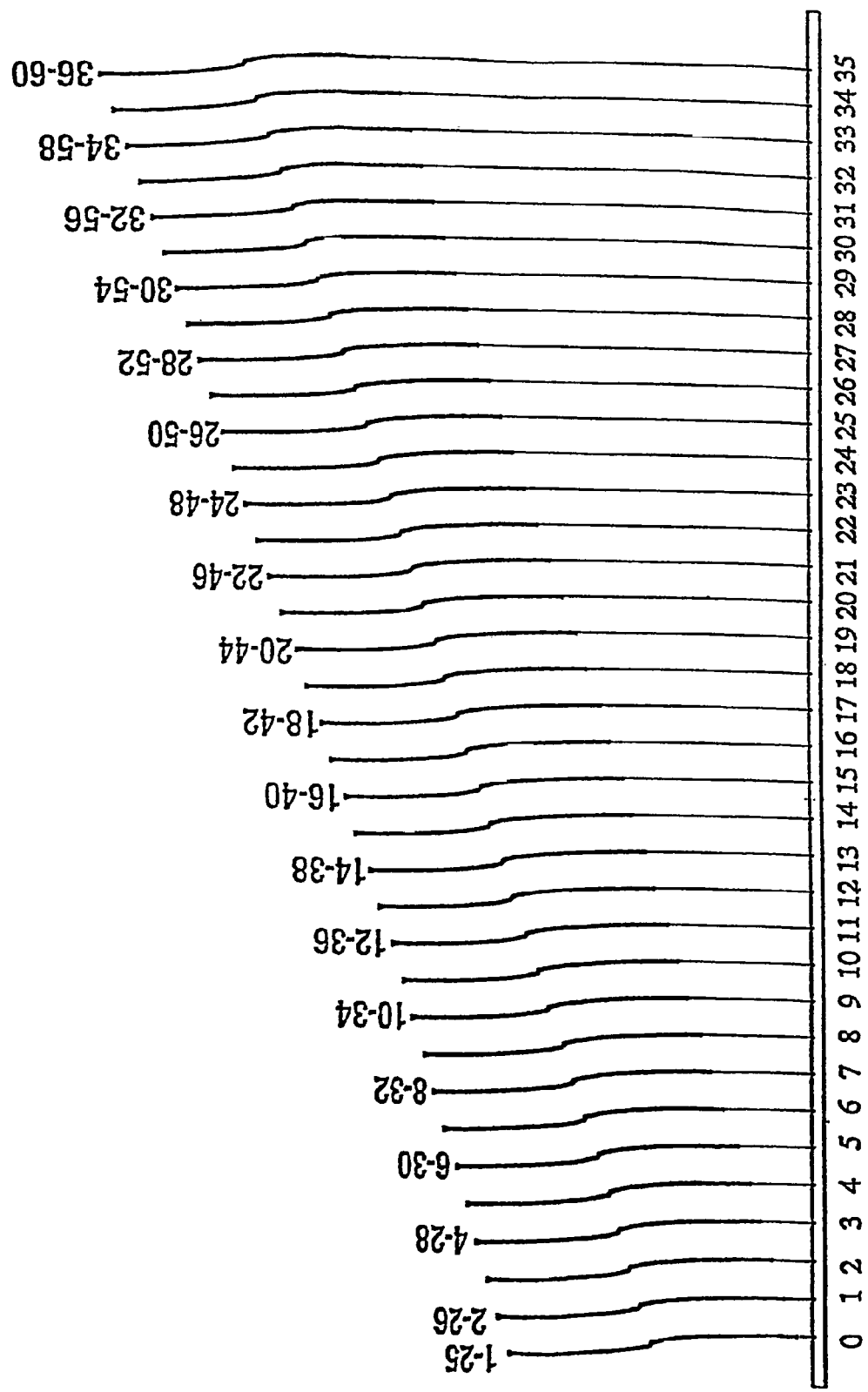

Staggered start quality control probes are-depicted schematically in FIG. 3A. A series of 25 nucleotide predetermined binding sequences (depicted by a bold line) are synthesized directly on the microarray, with the synthesis individual probe(s) starting at every synthesis cycle (from synthesis cycle 1-36). Unlike the above strategy, no spacers are used so that all of the quality control probes are made up exclusively of predetermined binding sequence that are 25 oligonucleotides long. The only difference between the quality control probes is the cycle at which synthesis begins (the bold line depicts the quality control probe and the thin line depicts synthesis cycles that had no monomer deposited). The synthesis cycles that make up each quality control probe are listed above each probe in FIG. 3A. Should there be no synthesis defects during oligonucleotide microarray synthesis, then the reverse complement of the probe sequence should hybridize equally well to all of the quality control probes and give comparable signals.

Figure 3B:
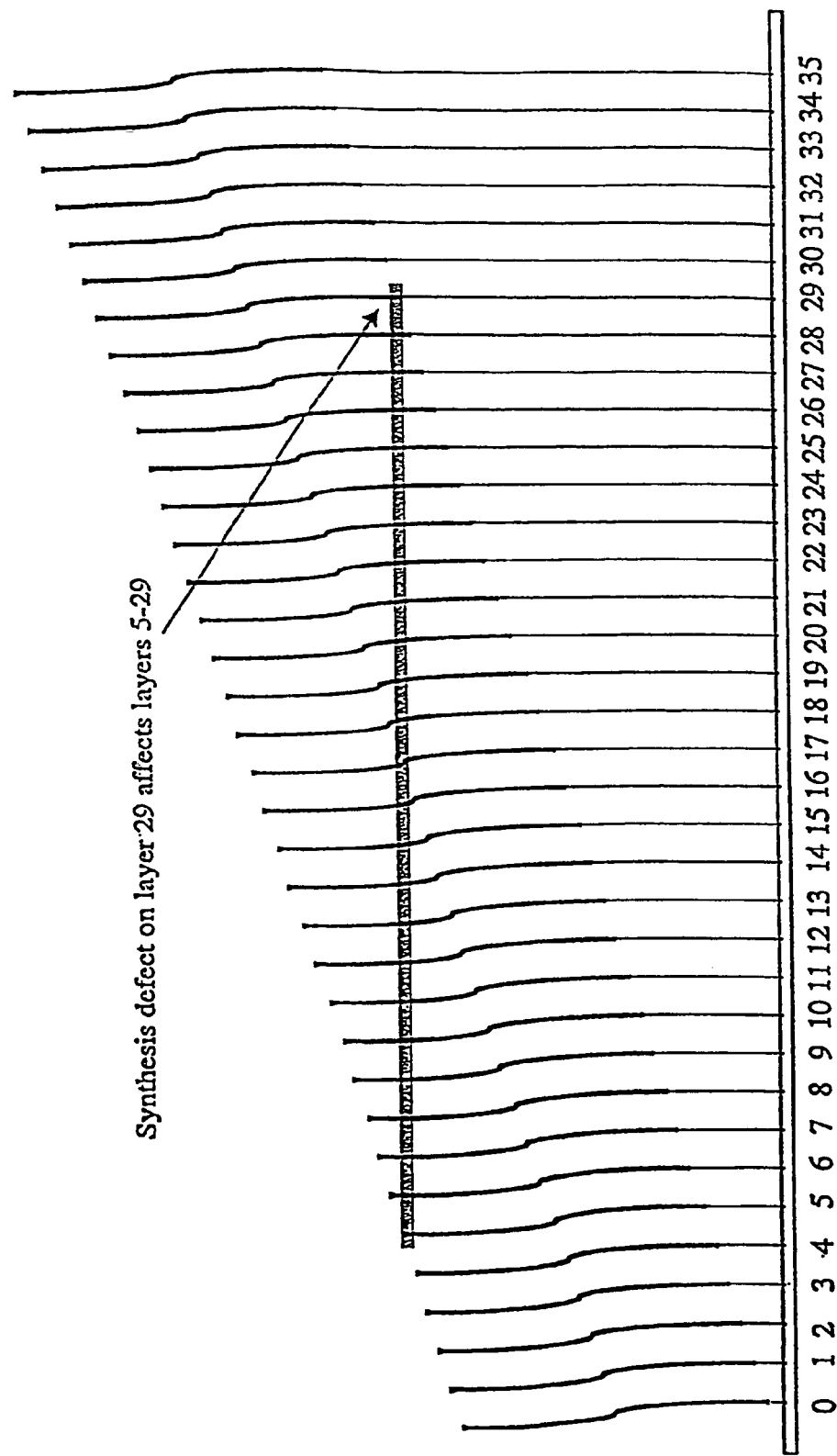

FIG. 3B schematically depicts a synthesis defect in synthesis cycle 29 of the oligonucleotide microarray (depicted by the gray bar). Because this affects all of the predetermined binding sequences that have synthesis cycle 29 as part of their sequence (i.e., those quality control probes that begin at synthesis cycles 5-29), hybridization of the reverse complement will be decreased in these quality control probes when compared to the level of binding that is observed with no synthesis error. Quality control probes that do not contain a monomer deposited during synthesis cycle 29 (i.e., those quality control probes that begin synthesis at cycles 1-4 or 30-35) are unaffected, however, and thus they should hybridize to their reverse complement to the same degree as when no synthesis error was present.

A quality control probe having the sequence of SEQ ID NO:1 was synthesized on an ink jet oligonucleotide microarray using a staggered start. The quality control sequence was started at every progressive synthesis cycle from 1 to 35 during the synthesis of the microarray. The fluorescently labeled reverse complement of SEQ ID NO:1 was used to hybridize to the oligonucleotide microarray.

Figure 10A:
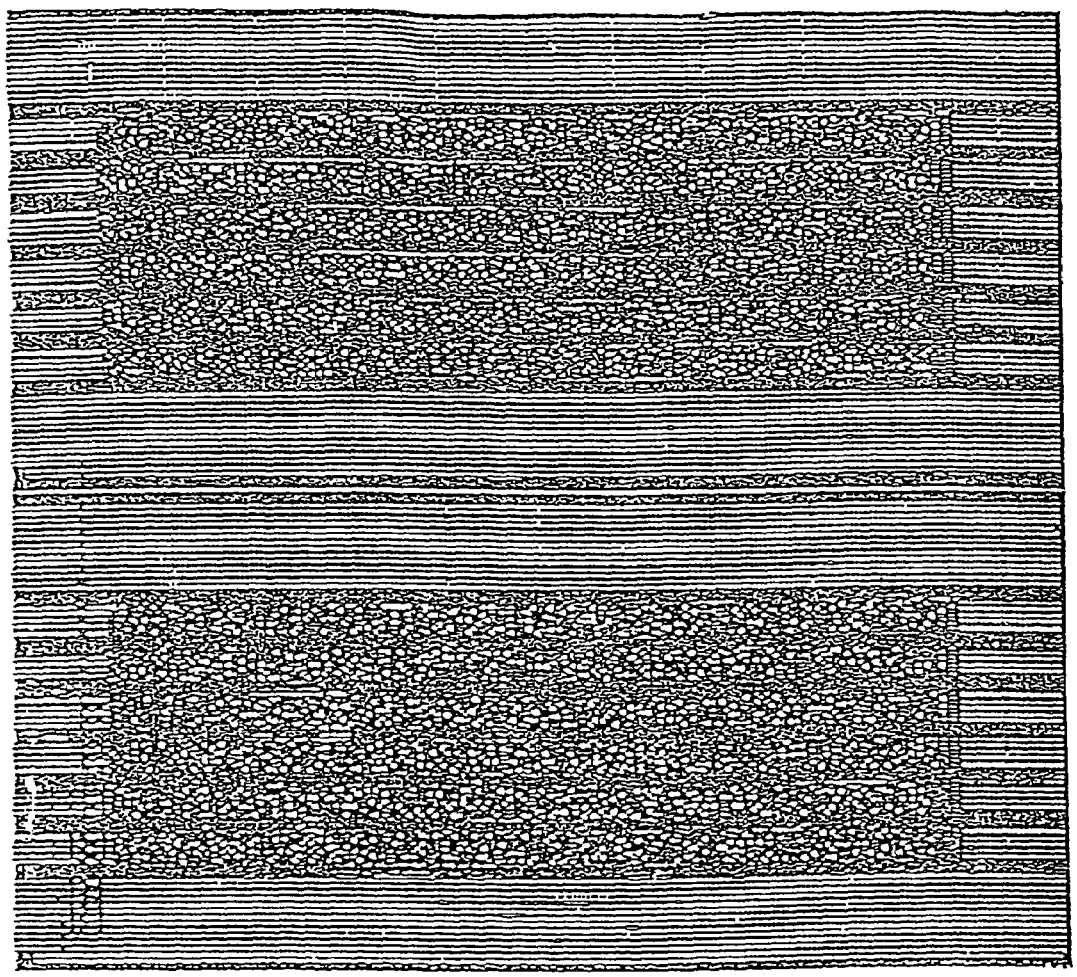
Figure 10B:
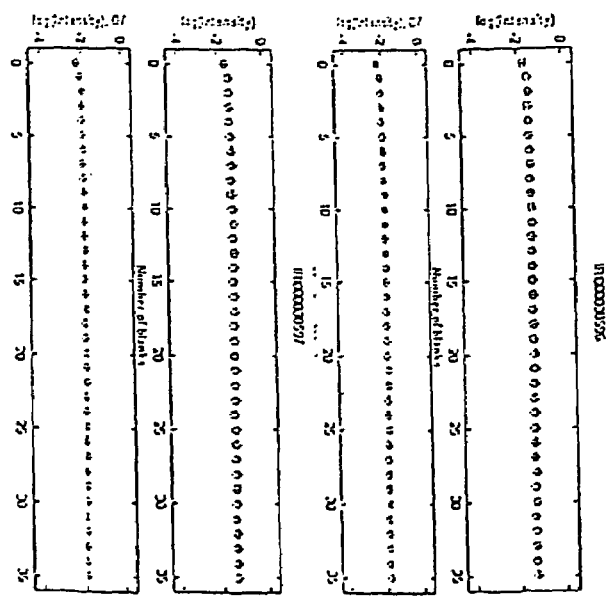
Figures 11A, 11B:
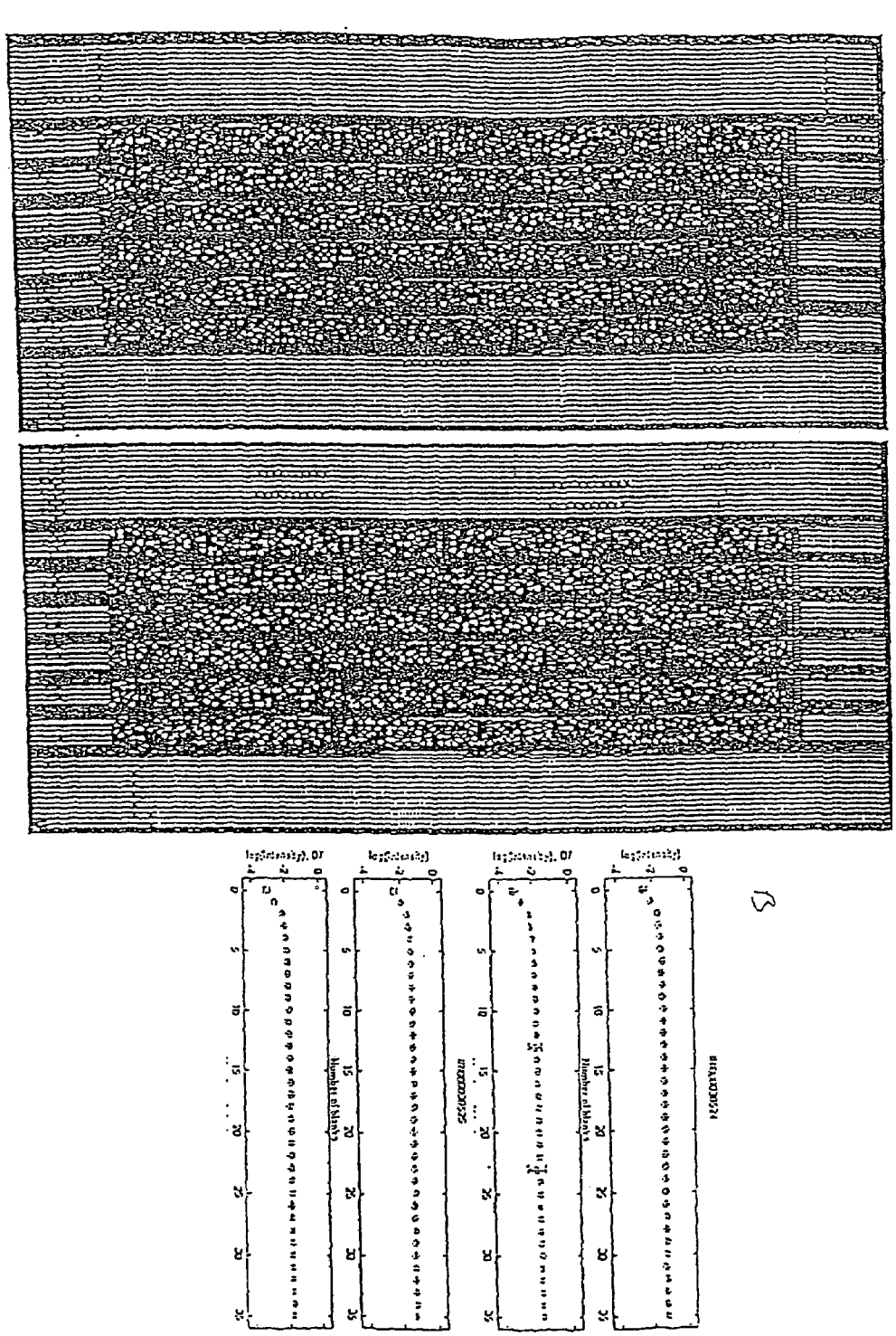
Figure 12A:
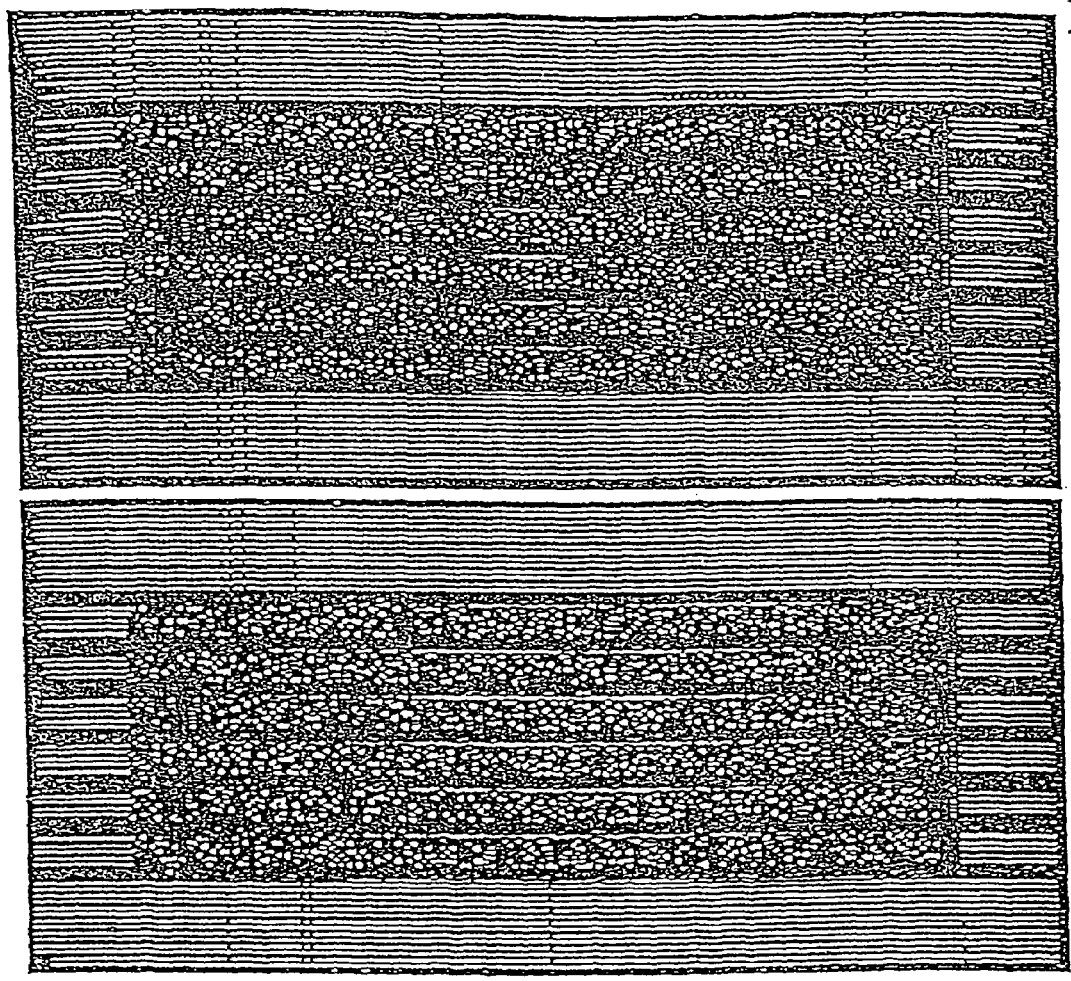
Figure 12B:
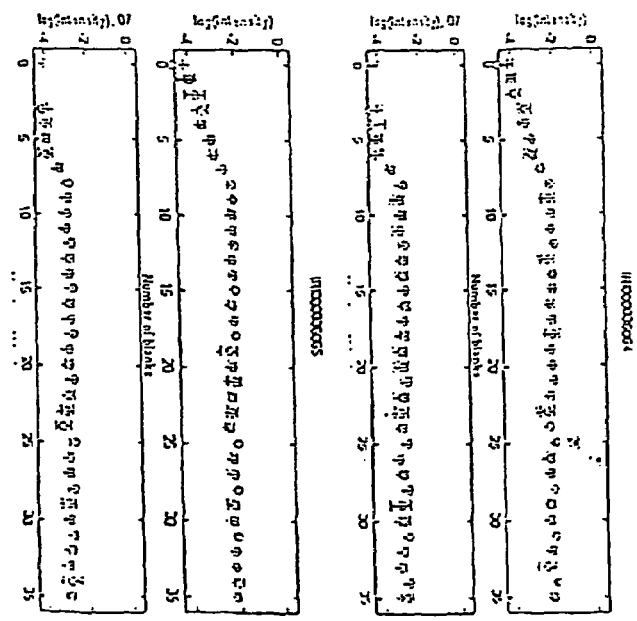
Figure 13A:
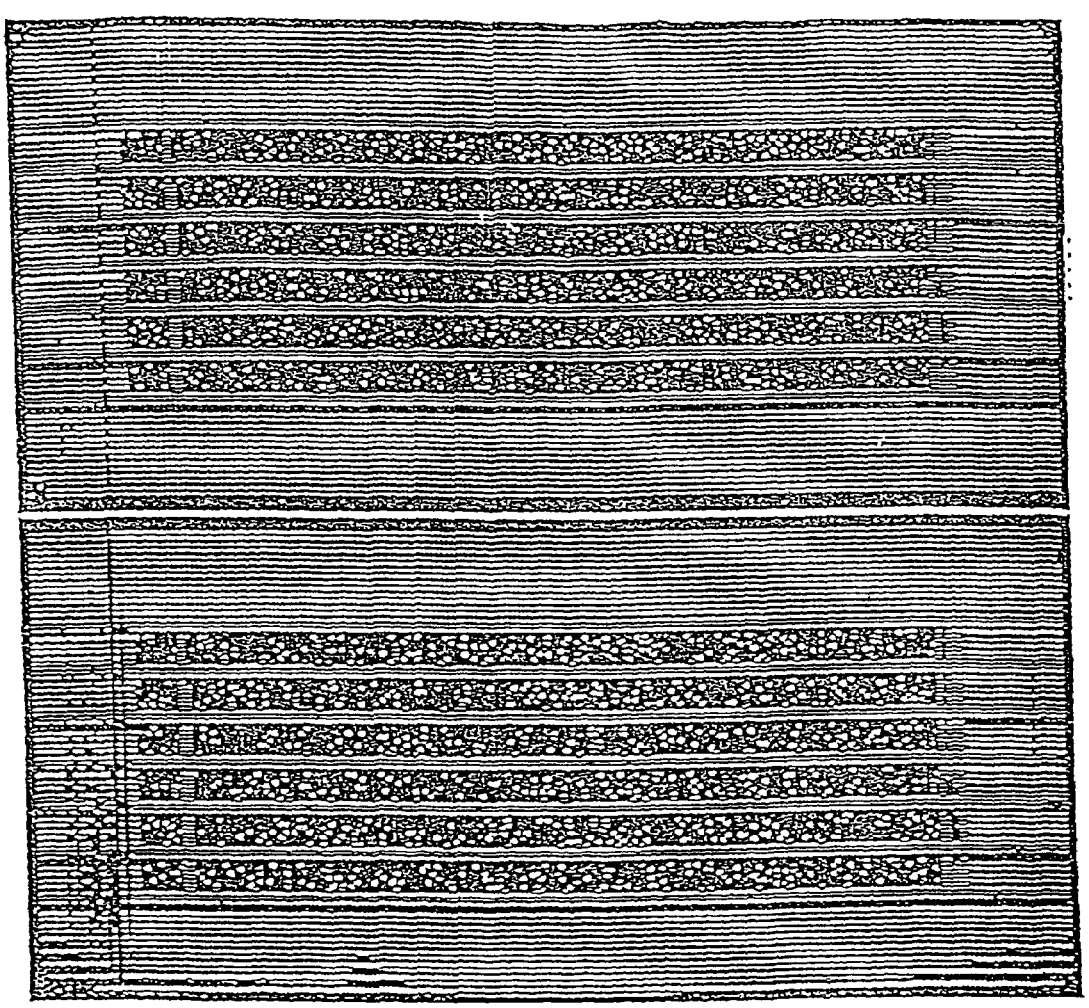
Figure 13B:
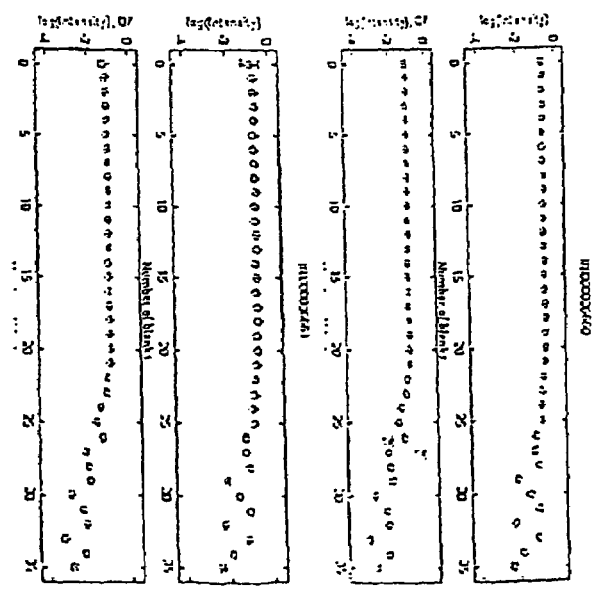

When there was inefficient synthesis in the first and second synthesis cycles during oligonucleotide microarray synthesis, only the first two staggered start quality control probes were affected (FIG. 10). The mean fluorescence intensity of the quality control probes at each synthesis cycle was plotted and showed a decrease in intensity only at probes that contained part of their quality control probe sequence at the first and/or second synthesis cycles of the microarray (FIG. 10B). All of the quality control probes that had synthesis that started subsequent to the second synthesis cycle were unaffected and hybridized to their reverse complement equally well. Similar results were seen when there was inefficient synthesis in the first five synthesis cycles (FIG. 11), the first eight synthesis cycles (FIG. 12), or the last fifteen synthesis cycles (FIG. 13) during oligonucleotide microarray synthesis. In each case, fluorescent intensity decreased only for quality control probes that had monomers that contributed part of the sequence deposited at the affected synthesis cycles of the microarray.

8. EXAMPLE 3

Increased Sensitivity of Quality Control Probes

8.1 Using Deletions

A synthesis failure during oligonucleotide microarray synthesis such that one or more synthesis cycles are compromised decreases the degree of binding of the quality control probe to its fluorescently labeled reverse complementary oligonucleotide (e.g., see, Sections 6.2 and 7.1 above). However, in instances where only a small number of synthesis cycles are compromised (i.e., one or two) such that the quality control probe is now slightly less than full length (i.e., a 24 mer or 23 mer relative to a full length 25 mer), binding to its reverse complementary oligonucleotide can still be relatively robust. In order to increase the sensitivity of synthesis failure detection, quality control probes with predetermined binding sequences already containing a single deletion were used in the methods of the invention. Such quality control probes had a predetermined binding sequence synthesized with a deletion in the nineteenth residue (from the 5' end) of SEQ ID NO:1. Any additional deletions due to a failure during microarray synthesis would exacerbate the defect and result in an increased deficiency in the ability to bind to the reverse complement of the full length 25 mer sequence. FIG. 14 shows that a single-deletion quality control probe on a microarray with synthesis defects in the thirty fourth and thirty fifth synthesis cycles is more sensitive than a quality control probe with no deletions.

5' ATCATCGTAGCTGGTCAGGTATCC 3'    (SEQ ID NO: 2)

Figures 14A, 14B:
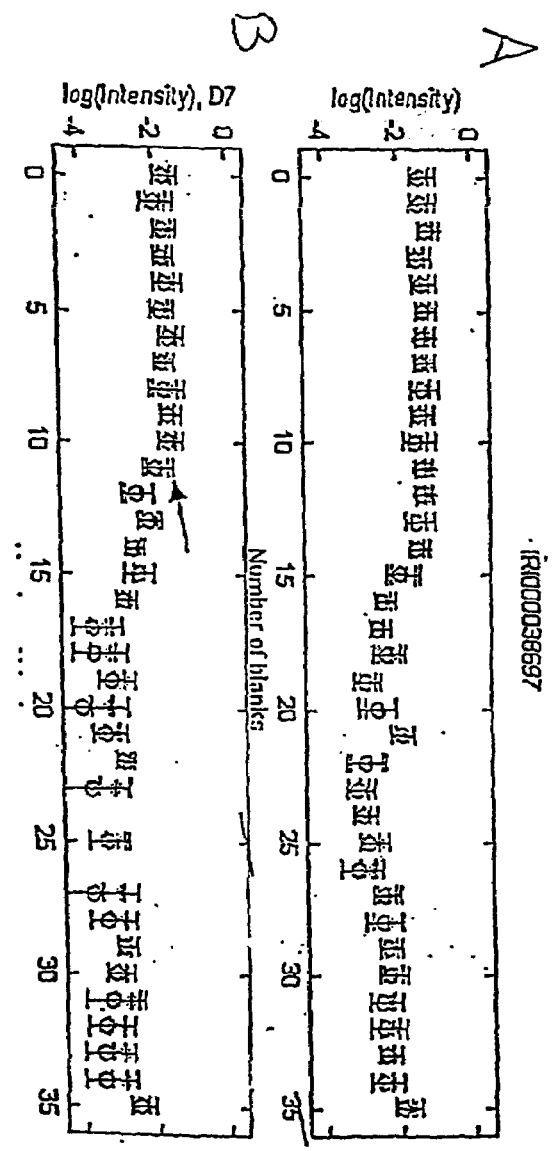

Labeled reverse complement of the full-length 25 nucleotide predetermined binding sequence was used to hybridize with quality control probes on each microarray. The mean fluorescence intensity plot of the quality control probes at each synthesis cycle was determined for each microarray. The full length quality control probe shows a synthesis defect starting at the fifteenth synthesis cycle (FIG. 14A). The single-deletion quality control probe shows a synthesis error starting at the eleventh synthesis cycle (FIG. 14B). Thus the single-deletion quality control probe is a more sensitive measure of microarray quality.

8.2 In Comparison with Correlation Plots

Figures 15A, 15B:
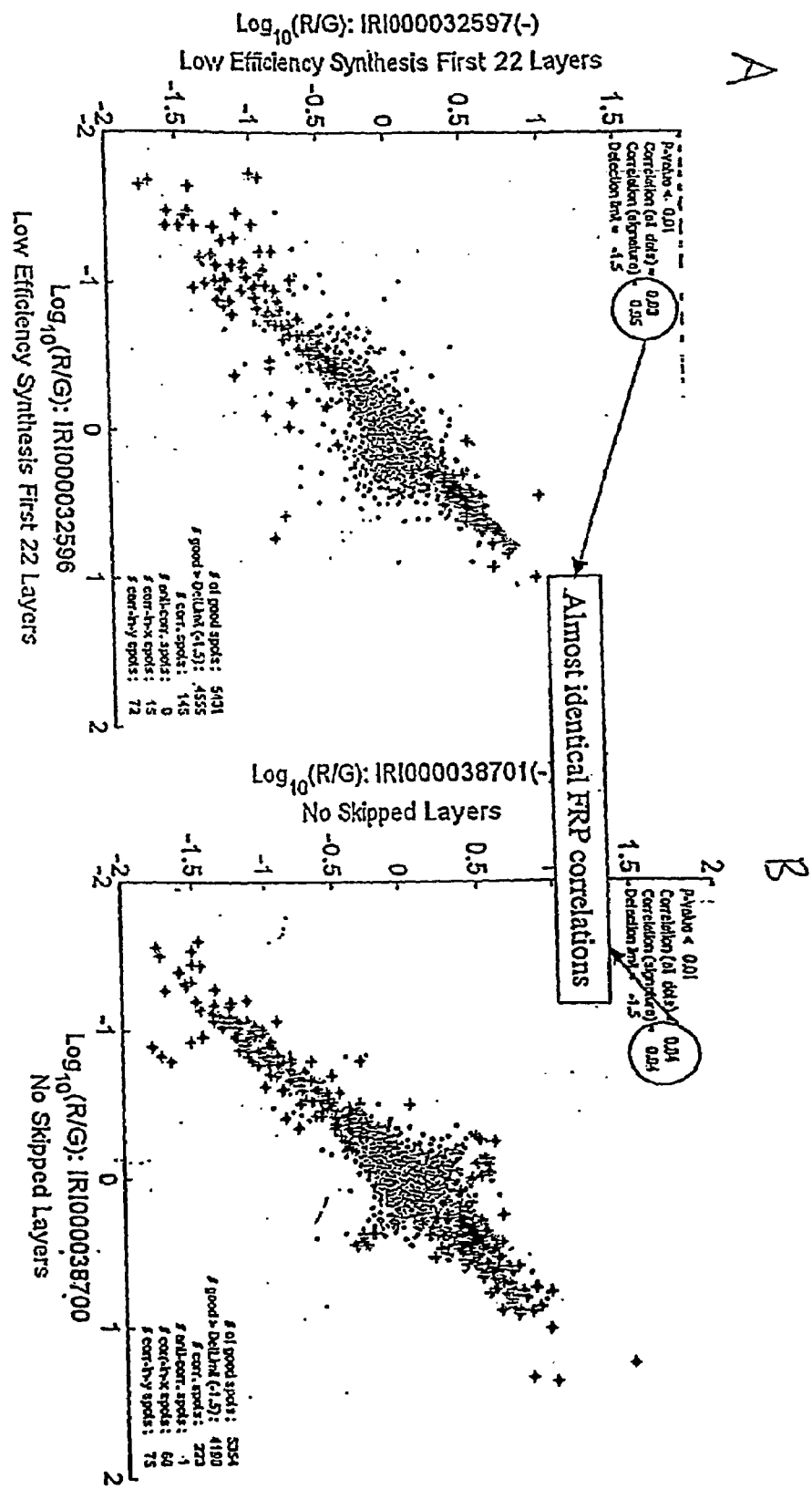
FIGS. 15A-15C illustrate correlations between fluor reversed pairs for a microarray that had skipped the first twenty two synthesis cycles during synthesis (A); a microarray that had no synthesis defect (B); and a microarray that had skipped the first twenty two synthesis cycles during synthesis with a microarray that had no synthesis defect (C).
Figure 15C:
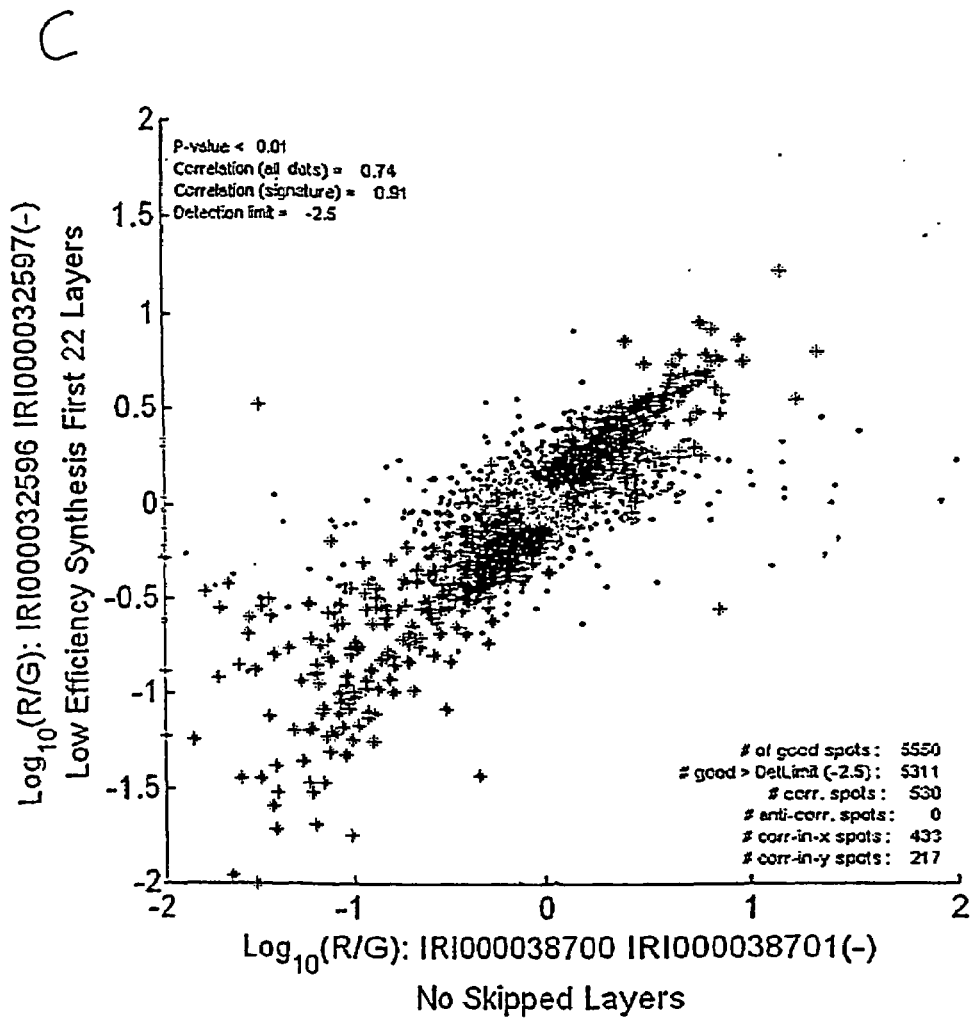
Figures 16A, 16B, 16C, 16D:
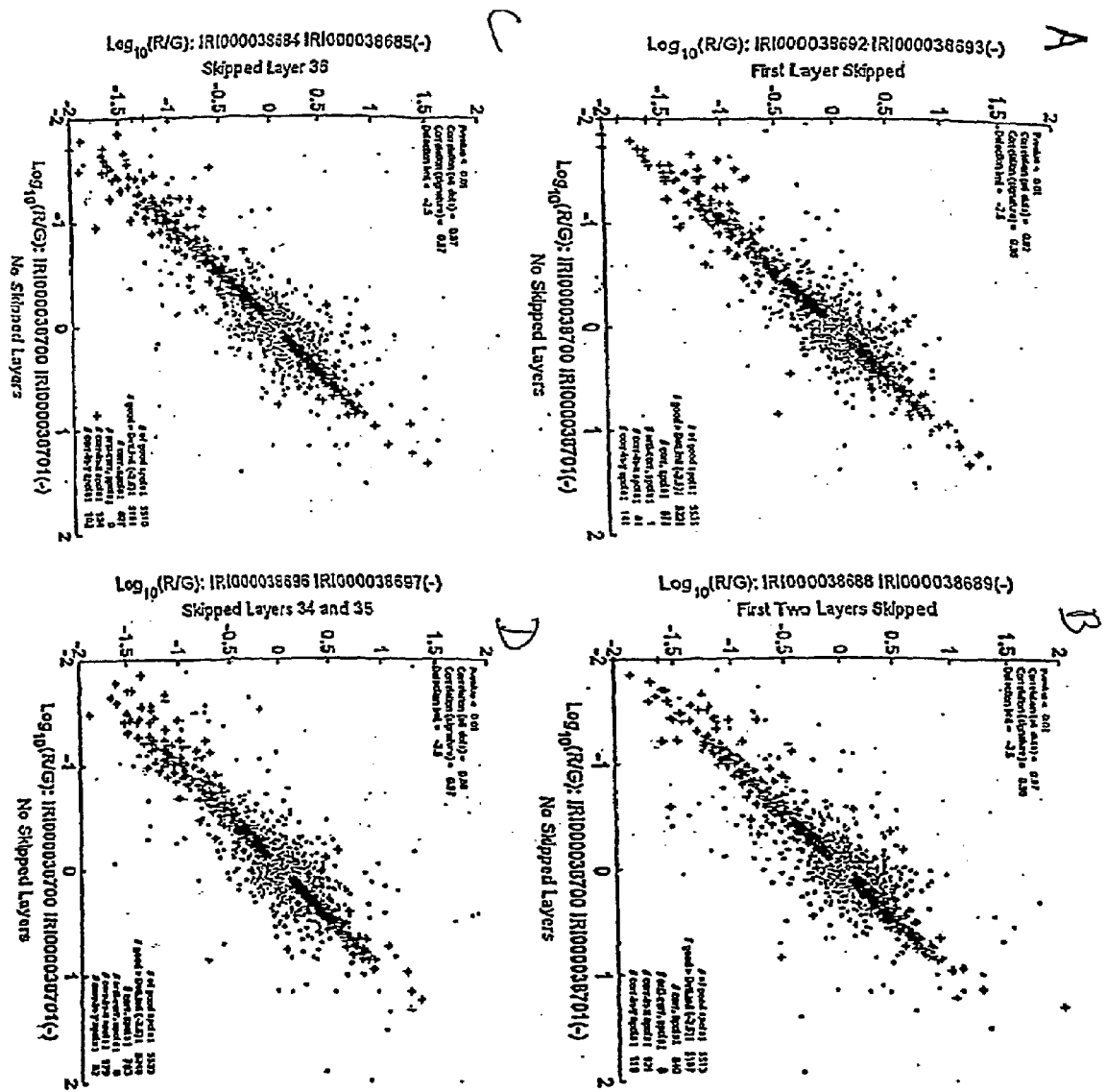
FIGS. 16A-16D illustrate correlations between oligonucleotide microarrays that had no synthesis defects with oligonucleotide microarrays that had the first (A), first and second (B), thirty sixth (C), or thirty fourth and thirty fifth (D) synthesis cycles skipped during synthesis.

These experiments show that using microarrays that contain one or more defects can provide data that, on the surface, looks acceptable. However, when the data is compared to data from microarrays with no defects, the problems become apparent. Correlation plots assess the quality of the data by examining the reproducibility of an experiment (e.g., using fluor-reversed pair analysis). Correlations between fluor reversed pairs were plotted for microarrays that had defects in the first twenty two synthesis cycles (FIG. 15A) and microarrays that had no synthesis defects (FIG. 15B). Oligonucleotides were labeled with either red or green fluorescent dye and a mixture was used to hybridize to each microarray. The log 10 of the ratio of red to green fluorescent signal was plotted against the log 10 of the ratio of red to green fluorescent signal for a duplicate chip. When data from a microarray with the first 22 cycles of synthesis skipped was compared to itself no problem was detected (FIG. 15A). Similarly, when data from a non-defective microarray was compared to itself no problem was detected (FIG. 15B). However, when data from a microarray with the first 22 cycles of synthesis skipped was compared to the data from a non-defective microarray, there is a difference (FIG. 15C). Even a defective microarray will result in data. Because it is not known beforehand what the data should look like, the data from defective arrays may initially look acceptable. The use of quality control probes according to the invention safeguards against using poor quality data Similar experiments were conducted with oligonucleotide microarrays that had the first (FIG. 16A), first and second (FIG. 16B), thirty sixth (FIG. 16C), or thirty fourth and thirty fifth (FIG. 16D) synthesis cycles skipped during synthesis. Data from oligonucleotide hybridization to the defective microarrays were plotted against data from non-defective microarrays. Again the plots all look similar and no synthesis defect would have been detected. This demonstrates that analysis of microarrays with correlation plots is not sensitive enough to identify defective microarrays.

9. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

---

---

What is claimed:

1. A method of determining if a positionally-addressable biopolymer array has a synthesis defect, said method comprising the following steps in the order stated:
   a) contacting a positionally-addressable biopolymer array with a sample, wherein said positionally addressable biopolymer array comprises a substrate to which is attached a plurality of different biopolymer probes, said different biopolymer probes being situated at different positions on said substrate and being the product of a step-by-step synthesis of said different biopolymer probes on said substrate, said plurality of different biopolymer probes comprising a plurality of quality control probes, each quality control probe in said plurality of quality control probes comprising (i) the same predetermined binding sequence or (ii) a different predetermined binding sequence with the same binding specificity, the synthesis of said predetermined binding sequence in each said quality control probe having been initiated during said step-by-step synthesis at different cycles of synthesis, wherein at least some of said quality control probes further comprise a first sequence contiguous with said predetermined binding sequence, wherein at least some of said quality control probes differ from other of said quality control probes in the length of said first sequence, and wherein said first sequence is a sequence of up to N monomers, where N is a whole number equal to or greater than 1, and wherein said sample comprises a binding partner that binds said predetermined binding sequence;

b) detecting or measuring binding between (1) two or more quality control probes of said plurality of quality control probes that differ in the number of said monomers; and (2) said binding partner in the sample; and c) comparing binding of said two or more quality control probes of said plurality of quality control probes; wherein if said binding is similar, the absence of a synthesis defect between said different cycles of synthesis used to synthesize said two or more quality control probes is indicated.

2. The method of claim 1 wherein said comparing comprises determining the binding ratio of two quality control probes of said two or more quality control probes, wherein said binding ratio is the amount of binding of a first quality control probe of said two quality control probes with said binding partner, divided by the amount of binding of a second quality control probe of said two quality control probes with said binding partner, and wherein said binding ratio being between 0.5 and 2.0 indicates the absence of said synthesis defect.

3. The method of claim 1 further comprising before step (a) a step of synthesizing said array.

4. The method of claim 1 wherein said sample comprises (A) total cellular RNA or mRNA from one or more cells or a plurality of nucleic acids derived therefrom, and (B) said binding partner, wherein said binding partner is not expressed by said one or more cells.

5. The method of claim 1 wherein said synthesis defect is a nozzle failure.

6. A method of detecting a nozzle failure using a positionally addressable array, said method comprising the following steps in the order stated:

a) contacting a positionally addressable array with a sample, wherein said positionally addressable array comprises a substrate to which is attached a plurality of different biopolymer probes, said different biopolymer probes being situated at different positions on said substrate and being the product of a step-by-step synthesis of said different biopolymer probes on said substrate, said plurality of different biopolymer probes comprising a plurality of quality control probes, each quality control probe in said plurality of quality control probes comprising (i) the same predetermined binding sequence or (ii) a different predetermined binding sequence with the same binding specificity, the synthesis of said predetermined binding sequence in each said quality control probe having been initiated during said step-by-step synthesis at different cycles of synthesis, wherein said sample comprises a binding partner that binds said predetermined binding sequence, wherein at least a portion of said plurality of quality control probes is arranged in a periodicity of P, wherein said periodicity of P is equal to the number of nozzles in an inkjet printhead, and wherein said array is synthesized by step-by-step synthesis using said inkjet printhead with P nozzles, wherein P is a whole number equal to or greater than 1;

b) detecting or measuring binding between two or more quality control probes of said plurality of quality control probes that are arranged in said periodicity of P and said binding partner in the sample; and c) comparing binding of said two or more quality control probes of said plurality of quality control probes in said periodicity of P, wherein if said binding is similar, the absence of a nozzle defect is indicated.

7. The method of claim 6 further comprising before step (a) a step of synthesizing said array.

8. The method of claim 6 wherein said sample comprises (A) total cellular RNA or mRNA from one or more cells or a plurality of nucleic acids derived therefrom, and (B) said binding partner, wherein said binding partner is not expressed by said one or more cells.

9. The method of claim 6 wherein P equals 20.

10. A method of determining if a positionally-addressable biopolymer array has a synthesis defect, said method comprising the following steps in the order stated:

a) contacting a positionally-addressable biopolymer array with a sample, wherein said positionally addressable biopolymer array comprises a substrate to which is attached a plurality of different biopolymer probes, said different biopolymer probes being situated at different positions on said substrate and being the product of a step-by-step synthesis of said different biopolymer probes on said substrate, said plurality of different biopolymer probes comprising a plurality of quality control probes, wherein the sequence of each quality control probe in said plurality of quality control probes consists of (i) the same predetermined binding sequence or (ii) a different predetermined binding sequence with the same binding specificity, the synthesis of said predetermined binding sequence in each said quality control probe having been initiated during said step-by-step synthesis at different cycles of synthesis of staggered start, wherein said respective different cycles of synthesis of staggered start are initiated at every progressive synthesis cycle during synthesis of the array, and wherein said sample comprises a binding partner that binds said predetermined binding sequence;

b) detecting or measuring binding between two or more quality control probes of said plurality of quality control probes and said binding partner in the sample; and c) comparing binding of said two or more quality control probes of said plurality of quality control probes, wherein if said binding is similar, the absence of a synthesis defect between said different cycles of synthesis of said array is indicated.

11. The method of claim 10 further comprising before step (a) a step of synthesizing said array.

12. The method of claim 10 wherein said sample comprises (A) total cellular RNA or mRNA from one or more cells or a plurality of nucleic acids derived therefrom, and (B) said binding partner, wherein said binding partner is not expressed by said one or more cells.

13. The method of claim 10 wherein said synthesis defect is a nozzle failure.

14. The method of claim 10 wherein said comparing comprises determining the binding ratio of two quality control probes of said two or more quality control probes, wherein said binding ratio is the amount of said binding partner bound to a first quality control probe of said two quality control probes, divided by the amount of said binding partner bound to a second quality control probe of said two quality control probes, and wherein said binding ratio being between 0.5 and 2.0 indicates the absence of said synthesis defect.

15. A method of detecting a nozzle failure using a positionally addressable array, said method comprising the following steps in the order stated:
- a) contacting a positionally addressable array with a sample, wherein said positionally addressable array comprises a substrate to which is attached a plurality of different biopolymer probes, said different biopolymer probes being situated at different positions on said substrate and being the product of a step-by-step synthesis of said different biopolymer probes on said substrate, said plurality of different biopolymer probes comprising a plurality of quality control probes, wherein the sequence of each quality control probe in said plurality of quality control probes consists of (i) the same predetermined binding sequence or (ii) a different predetermined binding sequence with the same binding specificity, the synthesis of said predetermined binding sequence in each said quality control probe having been initiated during said step-by-step synthesis at different cycles of synthesis of staggered start, wherein said respective different cycles of synthesis of staggered start are initiated at every progressive synthesis cycle during synthesis of the array, and wherein said sample comprises a binding partner that binds said predetermined binding sequence, wherein at least a portion of said plurality of quality control probes is arranged in a periodicity of P, wherein said periodicity of P is equal to the number of nozzles in an inkjet printhead, and wherein said array is synthesized by step-by-step synthesis using said inkjet printhead with P nozzles, wherein P is a whole number equal to or greater than 1;
- b) detecting or measuring binding between two or more quality control probes of said plurality of quality control probes that are arranged in said periodicity of P and said binding partner in the sample; and
- c) comparing binding of said two or more quality control probes of said plurality of quality control probes arranged in said periodicity of P, wherein if said binding is similar, the absence of a nozzle defect is indicated.

16. The method of claim 15 wherein P equals 20.

17. A method of detecting a nozzle failure using a positionally addressable array, said method comprising the following steps in the order stated:
- a) contacting a positionally-addressable biopolymer array with a sample, wherein said positionally addressable biopolymer array comprises a substrate to which is attached a plurality of different biopolymer probes, said different biopolymer probes being situated at different positions on said substrate and being the product of a step-by-step synthesis of said different biopolymer probes on said substrate, said plurality of different biopolymer probes comprising a plurality of quality control probes, each quality control probe in said plurality of quality control probes comprising (i) the same predetermined binding sequence or (ii) a different predetermined binding sequence with the same binding specificity, the synthesis of said predetermined binding sequence in each said quality control probe having been initiated during said step-by-step synthesis at different cycles of synthesis, wherein
    - at least some of said plurality of quality control probes further comprise a first sequence contiguous with said predetermined binding sequence,
    - at least some of said plurality of quality control probes differ from other of said plurality of quality control probes in the length of said first sequence,
    - said first sequence is a sequence of up to N monomers, where N is a whole number equal to or greater than 1,
    - at least a portion of said plurality of quality control probes is arranged in a periodicity of P, wherein said periodicity of P is equal to the number of nozzles in an inkjet printhead,
    - said array is synthesized by step-by-step synthesis using said inkjet printhead with P nozzles,
    - P is a whole number equal to or greater than 1, and
    - wherein said sample comprises a binding partner that binds said predetermined binding sequence;
- b) detecting or measuring binding between (1) two or more quality control probes of said plurality of quality control probes that are arranged in said periodicity of P and that differ in the number of said monomers; and (2) said binding partner in the sample; and
- c) comparing binding of said two or more quality control probes of said plurality of quality control probes arranged in said periodicity of P, wherein if said binding is similar, the absence of a nozzle defect is indicated.

18. The method of claim 17 wherein P equals 20.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
atcatcgtag ctggtcagtg tatcc                                    25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 2
atcatcgtag ctggtcaggt atcc                                     24